United States Patent
Berger et al.

(10) Patent No.: US 7,449,460 B2
(45) Date of Patent: Nov. 11, 2008

(54) 3-QUINOLINECARBONITRILE PROTEIN KINASE INHIBITORS

(75) Inventors: Dan Maarten Berger, New City, NY (US); Dennis William Powell, Cortlandt Manor, NY (US); Biqi Wu, Nanuet, NY (US)

(73) Assignee: Wyeth, Madison, NJ (US)

( * ) Notice: Subject to any disclaimer, the term of this patent is extended or adjusted under 35 U.S.C. 154(b) by 617 days.

(21) Appl. No.: 11/059,146

(22) Filed: Feb. 16, 2005

(65) Prior Publication Data

US 2005/0187247 A1 Aug. 25, 2005

Related U.S. Application Data

(60) Provisional application No. 60/546,511, filed on Feb. 20, 2004.

(51) Int. Cl.
*A61K 31/445* (2006.01)
*A61K 31/496* (2006.01)
*A61K 31/501* (2006.01)
*C07D 211/68* (2006.01)
*C07D 241/02* (2006.01)

(52) U.S. Cl. ............... 514/233.5; 514/252.11; 514/318; 544/109; 544/357; 546/194

(58) Field of Classification Search ............. 514/233.5, 514/252.11, 318; 544/109, 357; 546/194
See application file for complete search history.

(56) References Cited

U.S. PATENT DOCUMENTS

| 6,002,008 | A | 12/1999 | Wissner et al. |
|---|---|---|---|
| 6,288,082 | B1 | 9/2001 | Wissner et al. |
| 6,297,258 | B1 | 10/2001 | Wissner et al. |
| 6,780,996 | B2 | 8/2004 | Boschelli et al. |
| 2002/0026052 | A1 | 2/2002 | Boschelli et al. |

FOREIGN PATENT DOCUMENTS

| EP | 0 787 722 A1 | 8/1997 |
|---|---|---|
| WO | WO 96/09294 | 3/1996 |
| WO | WO 98/02437 | 1/1998 |
| WO | WO 98/02438 | 1/1998 |
| WO | WO 98/43960 | 10/1998 |
| WO | WO 00/51991 | 9/2000 |
| WO | WO 00/68201 | 11/2000 |
| WO | WO 01/12227 A1 | 2/2001 |
| WO | WO 01/68186 A2 | 9/2001 |
| WO | WO 02/36570 A1 | 5/2002 |
| WO | WO 02/44166 A1 | 6/2002 |
| WO | WO 02/083112 A2 | 10/2002 |

OTHER PUBLICATIONS

Wissner, A., et al.; J. Med. Chem. 43:3244-3256 (2000).
Wang, Y.D., et al.; Bioorg. & Med. Chem. Ltr. 10:2477-2840 (2000).
Zhang, N., et al.; Bioorg. & Med. Chem. Ltr. 10:2825-2828 (2000).
Boschelli, D.H., et al.; J. Med. Chem. 44:822-833 (2001).
Zhang, N., et al.; Bioorg. & Med. Chem. Ltr. 11:1407-1410 (2001).
Boschelli, D.H., et al.; J. Med. Chem. 44:3965-3977 (2001).
Zhang, N., et al.; Bioorg. & Med. Chem. Ltr. 12:423-425 (2002).
Boschelli, D.H., et al.; Bioorg. & Med. Chem. Ltr. 12:2011-2014 (2002).
Berger D et al., Substituted 4-Anilino-7-phenly-3-quinolinecarbonitriles as Src Kinase Inhibitors, Bioorg. Med. Chem. Lett.12:2989-2992 (2002).

*Primary Examiner*—Taofiq A Solola
(74) *Attorney, Agent, or Firm*—David Rubin

(57) ABSTRACT

This invention provides a compound of Formula 1

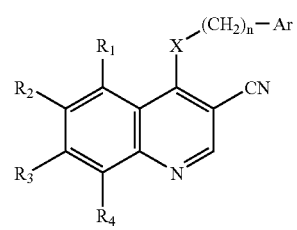

where Ar, X, $R_1$, $R_2$, $R_3$, and $R_4$ are defined herein, or a pharmaceutically acceptable salt thereof useful in the prevention or inhibition of diseases associated with the Ras/Raf/MEK signaling cascade in a mammal, such as neoplasms, strokes, osteoporosis, cancer, rheumatoid arthritis, inflammatory disease, polycystic kidney disease, and colonic polyps, and methods of making the compounds of formula 1 and intermediates.

8 Claims, No Drawings

3-QUINOLINECARBONITRILE PROTEIN KINASE INHIBITORS

This application claims priority from copending provisional application Ser. No. 60/546,511, filed Feb. 20, 2004, the entire disclosure of which is hereby incorporated by reference.

BACKGROUND OF THE INVENTION

This invention relates to substituted 3-quinolinecarbonitrile compounds as well as the pharmaceutically acceptable salts thereof. The compounds of the present invention inhibit the action of certain enzymes known as protein kinases. Protein kinases play a vital role as key regulators of a variety of critical cell functions. These enzymes function by catalyzing the transfer of a phosphate group from ATP to amino acid residues of substrate proteins. Tumorigenesis has been linked to the aberrant function of protein kinases and protein kinases are of particular interest as potential targets for anticancer agents.

Protein kinases are a class of enzymes that catalyze the transfer of a phosphate group from ATP to a tyrosine, serine, threonine, or histidine residue located on a protein substrate. Protein kinases clearly play a role in normal cell growth. Many of the growth factor receptor proteins function as kinases and it is by this process that they effect signaling. The interaction of growth factors with these receptors is a necessary event in normal regulation of cell growth. However, under certain conditions, as a result of either mutation or over expression, these receptors can become deregulated. Specific protein kinases have been implicated in diverse conditions including cancer (Traxler, P. M., *Exp. Opin. Ther. Patents,* 8, 1599 (1998); Bridges, A. J., *Emerging Drugs,* 3, 279 (1998)), restenosis (Mattsson, E., *Trends Cardiovas. Med.* 5, 200 (1995); Shaw, *Trends Pharmacol. Sci.* 16, 401 (1995)), atherosclerosis (Raines, E. W., *Bioessays,* 18, 271 (1996)), angiogenesis (Shawver, L. K., *Drug Discovery Today,* 2, 50 (1997); Folkman, J., *Nature Medicine,* 1, 27 (1995)) and osteoporosis (Boyce, *J. Clin. Invest.,* 90, 1622 (1992)).

One signaling pathway found in all eukaryotic organisms is the Ras-MAPK module, which is comprised of the Ras/Raf/MEK (mitogen-activated protein kinase kinase)/MAPK (mitogen-activated protein kinase) signaling cascade. This key pathway is involved in transmitting signals from growth factors and hormones at the extracellular compartment into the cytosol and to transcription factors in the nucleus. Alteration of the Ras-MAPK pathway is associated with the formation of certain human tumors.

Components of the Ras-MAPK Signaling Cascade

The Ras/Raf/MEK/MAPK signaling cascade is activated by GTP loading of Ras, which occurs in response to stimuli from cell surface receptors (Malumbres, M., Barbacid, M. *RAS oncogenes: the first 30 years.* Nat Rev Cancer 2003, 3: 459-65; Downward, J. *Targeting RAS signalling pathways in cancer therapy.* Nat Rev Cancer 2003, 3: 11-22; Bos, J. L. *Ras oncogenes in human cancer: A review.* Cancer Res 1989, 49: 4682-4689). Ras is a member of a large family of small (21 kDa) GTPases that act as molecular switches in the regulation of cell growth, differentiation, survival, and apoptosis (Malumbres, M., Barbacid, M. *RAS oncogenes: the first 30 years.* Nat Rev Cancer 2003, 3: 459-65; Downward, J. *Targeting RAS signalling pathways in cancer therapy.* Nat Rev Cancer 2003, 3: 11-22; Bos, J. L. *Ras oncogenes in human cancer: A review.* Cancer Res 1989, 49: 4682-4689; Shields, J. M., Pruitt, K., McFall, A. et al. *Understanding Ras: 'it ain't over 'til it's over'.* Trends Cell Biol 2000, 10: 147-154). Ras is initially defined as a component of oncogenic murine retroviruses (Ellis, R. W., Defeo, D., Shih, T. Y. et al. *The p21 src genes of Harvey and Kirsten sarcoma viruses originate from divergent members of a family of normal vertebrate genes.* Nature 1981, 292: 506-511), and it became the focus of intensive research in the early 1980s when the connection between mutant forms of Ras and human cancer was established (Ellis, R. W., Defeo, D., Shih, T. Y. et al. *The p21 src genes of Harvey and Kirsten sarcoma viruses originate from divergent members of a family of normal vertebrate genes.* Nature 1981, 292: 506-511; Perucho, M., Goldfarb, M., Shimizu, K., Lama, C., Fogh, J. and Wigler, M. *Human-tumor-derived cell lines contain common and different transforming genes.* Cell 1981, 27: 467-476; Santos, E., Martin-Zanca, D., Reddy, E. P., Pierotti, M. A., Della Porta, G., Barbacid, M. *Malignant activation of a K-ras oncogene in lung carcinoma but not in normal tissue of the same patient.* Science 1984, 223: 661-664). Ras mutations that lead to oncogenic activation occur primarily in two hotspots: Gly12 and Gln61 (Krengel, U., Schlichting, L., Scherer, A. et al. *Three-dimensional structures of H-ras p21 mutants: Molecular basis for their inability to function as signal switch molecules.* Cell 1990, 62: 539-548). The mutational changes at these residues found in human cancers impede the GTP hydrolysis activity of Ras, thus causing Ras to remain in the GTP-bound or "on" conformation. With this finding, a better appreciation of the molecular basis of aberrant signaling associated with ~30% of all human cancers are obtained.

There are three Ras isoforms associated with human cancer, H-Ras, N-Ras, and K-Ras; and of these, 95% are due to K-Ras mutations. Ras proteins are closely related, having 85% amino acid identity with a 20 amino acid variable region at the carboxy terminus (Lowy, D. R. and Willumsen, B. M. *Function and regulation of ras.* Annual Review of Biochemistry 1993, 62: 851-891). A Cysteine residue occurs in all Ras proteins after the variable region, and this is the site of post-translational modification of Ras by addition of a farnesyl isoprenoid lipid (Hancock, J. F., Magee, A. I., Childs, J. E. and Marshall, C. J. *All ras proteins are polyisoprenylated but only some are palmitoylated.* Cell 1989, 57: 1167-1177). All Ras proteins are further modified by proteolysis of the three carboxy terminal amino acids and subsequent methylation of the new carboxy terminus. These modifications stabilize Ras interaction with the inner cell membrane where it must reside to form a multi-protein complex with Raf, MEK, MAPK and scaffold proteins to activate signaling in the Ras-MAPK module (Kolch, W. *Meaningful relationships: The regulation of the Ras/Raf/MEK/ERK pathway by protein interactions.* Biochemical J 2000, 351 Pt 2: 289-305; Kolch, W. *Ras/Raf signalling and emerging pharmacotherapeutic targets.* Expert Opin Pharmaco 2002, 3: 709-718).

As the consequences of mutated Ras function were elucidated, this attracted sufficient attention from numerous pharmaceutical laboratories to initiate discovery and development programs for small molecule inhibitors of this signaling protein. The goal of these programs is to bring forward inhibitors of aberrant Ras signaling that have minimal associated toxicities. Numerous Ras inhibitors have been described, and they impair Ras-MAPK signaling by blocking proper post-translational modification of Ras by protein farnesyl transferase, thereby preventing membane localization. These Ras inhibitors have shown good pre-clinical efficacy, and are currently being evaluated in clinical trials. The sequential downstream kinase effectors of Ras, namely Raf, MEK, and MAPK are in addition viewed as equally attractive targets for the pharmacological intervention of cancer.

Raf proteins are fairly homologous (~60%). These 66-84 kDa serine/threonine kinases include A, B, and C isoforms (C-Raf=Raf1, c-Raf), which co-exist in many cell types and activate MEK (Kolch, W. *Ras/Raf signalling and emerging pharmacotherapeutic targets*. Expert Opin Pharmaco 2002, 3: 709-718; Chong, H., Vikis, H. G., Guan, K.-L. *Mechanisms of regulating the Raf kinase family*. Cell Signal 2003, 15: 463-469; Chong, H., Lee, J., Guan, K. L. *Positive and negative regulation of raf kinase activity and function by phosphorylation*. EMBO J 2001, 20: 3716-3727). Three conserved regions occur in Raf proteins: CR1 which is at the N-terminal and contains a Ras binding domain (RBD) and a cysteine rich domain (CRD); CR2 which contains a serine/threonine rich region; and CR3 which contains the catalytic kinase domain. GTP-loaded Ras recruits Raf to the inner cell membrane. This is crucial for Raf activation, though activation is a complex process not yet fully understood. For example, there are at least 13 regulatory phosphorylation sites on C-Raf (Fabian, J. R., Daar, I. O., Morrison, D. K. *Critical tyrosine residues regulate the enzymatic and biological activity of raf-1 kinase*. Mol Cell Biol 1993, 13: 7170-7179; Marais, R., Wynne, J., Treisman, R. *The SRF accessory protein Elk-1 contains a growth factor-regulated transcriptional activation domain*. Cell 1993, 73: 381-393; Morrison, D. K., Heidecker, G., Rapp, U. R. and Copeland, T. D. *Identification of the major phosphorylation sites of the Raf-1 kinase*. J Biol Chem 1993, 268: 17309-17316; Mason, C. S., Springer, C. J., Cooper, R. G., Superti-Furga, G., Marshall, C. J., Marais, R. *Serine and tyrosine phosphorylations cooperate in Raf-1, but not B-Raf activation*. EMBO J 1999, 18: 2137-2148; Dhillon, A. S., Meikle, S., Yazici, Z., Eulitz, M., Kolch, W. *Regulation of Raf-1 activation and signalling by dephosphorylation*. EMBO J 2002, 21: 64-71; Kolch, W. *To be or not to be: a question of B-Raf?* Trends Neurosci 2001, 24: 498-500; Abraham, D., Podar, K., Pacher, M. et al. *Raf-1-associated protein phosphatase 2A as a positive regulator of kinase activation*. J Biol Chem 2000, 275: 22300-22304; Yeung, K., Seitz, T., Li, S. et al. *Suppression of Raf-1 kinase activity and MAP kinase signalling by RKIP*. Nature 1999, 401: 173-177; Chang, F., Steelman, L. S., Lee, J. T. et al. *Signal transduction mediated by the Ras̃Rãf/MEKERK pathway from cytokine receptors to transcription factors: potential targeting for therapeutic intervention*. Leukemia 2003 17:1263-1293). Not only GTP-loaded Ras, but also various kinases (e.g. C-Tak1, PAK, PKC, PKA, Src), phosphatases (PP1, PP2A), adapter proteins, and scaffold proteins (KSR) are implicated in full Raf activation (Dhillon, A. S. and Kolch, W. *Untying the regulation of the Raf-1 kinase*. Arch Biochem Biophys 2002, 404: 3-9; Morrison, D. K. *KSR: a MAPK scaffold of the Ras pathway?* J Cell Sci 2001, 114: 1609-1612; Baccarini, M. *An old kinase on a new path: Raf and apoptosis*. Cell Death Differ 2002, 9: 783-785). The three Raf isoforms differ in their ability to interact with Ras isoforms, to activate MEK, and to transform rodent fibroblasts in vitro (Pritchard, C. A., Bolin, L., Slattery, R., Murray, R., McMahon, M. *Post-natal lethality and neurological and gastrointestinal defects in mice with targeted disruption of the A-Raf protein kinase gene*. Curr Biol 1996, 6: 614-617). The B-Raf isoform in all cases is the most active followed by C-Raf, and then A-Raf.

A, B, and C Raf knockout mice have been described (Wojnowski, L., Zimmer, A. M., Beck, T. W. et al. *Endothelial apoptosis in Braf-deficient mice*. Nat Genet 1997, 16: 293-297; Huser, M., Luckett, J., Chiloeches, A. et al. *MEK kinase activity is not necessary for Raf-1 function*. EMBO J 2001, 20: 1940-1951; Murakami, M. S., Morrison, D. K. *Raf-1 without MEK?* Science's Stke: Signal Transduction Knowledge Environment 2001, 2001: PE3). B-Raf deficient embryos die at mid-gestation due to apoptotic cell death in endothelial cells leading to vascular hemorrhage. C-Raf deficiency causes mid-gestational death due to more diffuse apoptotic tissue effects. A-Raf deficient mice are born alive, but show neurological and intestinal defects. These divergent phenotypes show that Raf isoforms serve distinct functions in different tissues. These studies have shown that individual B-Raf and C-Raf survival functions cannot be performed by other Raf isoforms. They also demonstrated that normal levels of MAPK activation occurs in C-Raf deficient mouse cells, indicating that the anti-apoptotic function of C-Raf is not mediated by the MAPK cascade.

The anti-apoptotic function of C-Raf may be mediated by antagonism of apoptosis-stimulated kinase 1 (ASK-1). There is evidence to suggest that C-Raf impedes ASK-1 function via a protein-protein interaction that is not associated with C-Raf kinase activity (Chen, J., Fujii, K., Zhang, L., Roberts, T., Fu, H. *Raf-1 promotes cell survival by antagonizing apoptosis signal-regulating kinase 1 through a MEK-ERK independent mechanism*. Proc Natl Acad Sci USA 2001, 98: 7783-7788). Raf also can impede apoptosis in a kinase dependent manner. For example, Raf/MEK/MAPK signaling activates Rsk1, which in turn phosphorylates and inactivates BAD, a pro-apoptotic protein (Shimamura, A., Ballif, B. A., Richards, S. A., Blenis, J. *Rsk1 mediates a MEK-MAP kinase cell survival signal*. Curr Biol 2000, 10: 127-135). Additionally, C-Raf can be localized to the mitochondria by a Bcl-2 mediated process, where it can inactivate pro-apoptotic proteins by phosphorylation (Wang, H. G., Miyashita, T., Takayama, S. et al. *Apoptosis regulation by interaction of Bcl-2 protein and Raf-1 kinase*. Oncogene 1994, 9: 2751-2756). Raf anti-apoptotic effects are complex and will require further study to clarify. However, this characteristic of Raf enhances its appeal as a pharmaceutical target since a hallmark of cancer cells is resistance to apoptosis which at least in part is likely attributable to improper Raf activation (Herrera, R., Sebolt-Leopold, J. S. *Unraveling the complexities of the Raf/MAP kinase pathway for pharmacological intervention*. Trends Mol Med 2002, 8: S27-31).

As with Ras, oncogenic forms of Raf have been found to be components of transforming murine retroviruses (Mark, G. E., Rapp, U. R. *Primary structure of v-raf: relatedness to the src family of oncogenes*. Science 1984, 224: 285-289). Oncogenic Raf in murine retroviruses results from N-terminal deletions that remove the regulatory sequences that control Raf kinase activity. Most recently, a systematic human genome-wide screening effort to detect alterations in genes that control cell proliferation, differentiation, and death found activating B-Raf mutations in 66% of malignant melanomas (Davies, H., Bignell, G. R., Cox, C. et al. *Mutations of the BRAF gene in human cancer*. Nature 2002, 417: 949-954). Additionally, B-Raf mutations are observed at lower frequencies in a wide range of other cancers including colorectal, lung, breast, and ovarian.

The significance of B-Raf mutations in colorectal tumors is extended in a subsequent study showing that mutations in either B-Raf or K-Ras (not both) are detected in a sample of colorectal tumors examined at all stages of development, including pre-malignant lesions (Rajagopalan, H., Bardelli, A., Lengauer, C., Kinzler, K. W., Vogelstein, B., Velculescu, V. E. *Tumorigenesis: RAF/RAS oncogenes and mismatch-repair status*. Nature 2002, 418: 934). The frequency of B-Raf mutations in these colorectal tumors is 10%, whereas the K-Ras mutation frequency is 51%. Cumulative K-Ras/B-Raf mutation frequency in colorectal cancer is therefore 61%. In the case of melanoma, an examination of N-Ras mutation (the Ras isoform mutated in melanoma), together with B-Raf has shown a cumulative mutation frequency of 81% (Smalley, K. S. *A pivotal role for ERK in the oncogenic behaviour of malignant melanoma?* Int J Cancer 2003, 104: 527-532). These statistics, when combined with the 2002 incidence of colorectal cancer (148,000) and melanoma (54,000) in the U.S. (American Cancer Society), make Raf a compelling pharmaceutical target.

MEK1 and MEK2 are expressed 43-46 kDa kinases activated by Raf phosphorylation of two serine residues (Ser217-Ser221). MEK1 and MEK2 are members of a larger family of dual specificity kinases (MEK1-7) that phosphorylate Threonine and Tyrosine residues within the TXY motif of various MAP kinases (Dhanasekaran, N., Premkumar Reddy, E. *Signaling by dual specificity kinases*. Oncogene 1998, 17:1447-1455). MEK1 and MEK2 are encoded by distinct genes, but they have high homology (80%) within the C-terminal catalytic kinase domain and most of the N-terminal regulatory domain (English, J., Pearson, G., Wilsbacher, J. et al. *New insights into the control of MAP kinase pathways*. Exp Cell Res 1999, 253: 255-270). At the N-terminus of MEK1 and MEK2 there are 30 amino acids of divergent sequence that may direct differential interactions with both activators and substrates. The only known substrates for MEK1/MEK2 are the MAPK1 and MAPK2, which they phosphorylate on Thr202/183 and Tyr204/185, respectively.

MEK1 deficient mice have been described, and inactivation of MEK1 leads to embryonic lethality due to decreased placental vascularization during embryogenesis (Giroux, S., Tremblay, M., Bernard, D. et al. *Embryonic death of Mek1-deficient mice reveals a role for this kinase in angiogenesis in the labyrinthine region of the placenta*. Curr Biol 1999, 9: 369-372). MEK1 deficiency is not compensated for by MEK2. In contrast, MEK2 deficient mice are viable and fertile, with no morphological alterations (Bélanger, L. F., Roy, S., Tremblay, M. et al. *Mek2 is dispensable for mouse growth and development*. Mol Cell Biol 2003, 23: 4778-4787). These data demonstrate that MEK2 is not necessary for the normal development of mouse embryos, indicating that the loss of MEK2 can be compensated for (Bélanger, L. F., Roy, S., Tremblay, M. et al. *Mek2 is dispensable for mouse growth and development*. Mol Cell Biol 2003, 23: 4778-4787) by at least in part MEK1.

Oncogenic forms of MEK1 or MEK2 have not been described in retroviruses or human cancers. However, a MEK1 where Ser218 and Ser222 are both mutated to Asp is capable of causing oncogenic transformation of various rodent fibroblast cell lines (Mansour, S. J., Matten, W. T., Hermann, A. S. et al. *Transformation of mammalian cells by constitutively active MAP kinase kinase*. Science 1994, 265: 966-970).

The MAPK components of the Ras-MAPK module have also been designated ERK1 and ERK2 (extracellular signal-regulated kinases). These MAPK isoforms (also designated p44 MAPK and p42 MAPK) are highly homologous (>80%), expressed 44-42 kDa serine/threonine kinases that are members of a larger gene family that includes ERK 1, 2, 3, 5, 7; JNK 1-3; and p38 α, β, γ, and δ. Experimental data indicate that ERK1 and ERK2 are functionally equivalent (English, J. M., Cobb, M. H. *Pharmacological inhibitors of MAPK pathways*. Trends Pharmacol Sci 2002, 23: 40-45). ERKs are activated by MEK phosphorylation of their TEY sequence; dual phosphorylation is required for activation, and in the case of ERK2 results in a >1000 fold increase in activity. Downstream substrates of ERK1/2 include cytoskeletal proteins, kinases, phosphatases, and transcription factors. The pleiotropic effects of MAPK activation on cell growth and differentiation are undoubtedly mediated through this diverse array of effectors.

No constitutively active MAP kinases are known, despite attempts at their genetic selection and site-directed mutagenesis. This failure suggests that cells cannot tolerate the continuous activation of MAP kinases. Among the kinase components of the Ras-MAPK signaling only the ERK2 atomic structure has been solved (Zhang, F., Strand, A., Robbins, D., Cobb, M. H., Goldsmith, E. J. *Atomic structure of the MAP kinase ERK2 at 2.3 resolution*. Nature 1994, 367: 704-711).

The ERK1/ERK2 components of the Ras-MAPK module are the most abundant (~$10^6$ molecules per cell). MEK also is relatively abundant in most cell types (~$3.5 \times 10^5$ molecules per cell), whereas Raf and Ras molecules are less abundant (~$2 \times 10^4$ per cell) (Ferrell, J. E., Jr. *Tripping the switch fantastic: how a protein kinase cascade can convert graded inputs into switch-like outputs*. Trends Biochem Sci 1996, 21: 460-466). All MAPK molecules can become fully activated in cells where only 10-50% of Ras molecules are GTP bound. The predicted sensitivity of the Raf/MEK1/MAPK signaling cascade to inhibitors is: Raf>MEK1>MAPK (Huang, C. Y., Ferrell, J. E., Jr. *Ultrasensitivity in the mitogen-activated protein kinase cascade*. Proc Natl Acad Sci USA 1996, 93: 10078-10083). This sensitivity profile results from the distributive (non-processive) mechanism of both Raf and MEK1 in which the rate of MEK1 activation depends on the concentration of Raf squared; and similarly the rate of MAPK activation is dependent on the concentration of MEK1 squared. To date, potent inhibitors of Raf and MEK, but not ERK, have been reported.

BRIEF SUMMARY OF THE INVENTION

This invention relates to substituted 3-quinolinecarbonitrile compounds useful for the treatment or inhibition of certain diseases that are the result of deregulation of these protein kinases. The compounds of this invention are anti-cancer agents and are useful for the treatment or inhibition of cancer in mammals. In addition, the compounds of this invention are useful for the treatment and inhibition of stroke, osteoporosis, rheumatoid arthritis and other inflammatory disorders, as well as polycystic kidney disease and colonic polyps.

In accordance with this invention there is provided a group of compounds represented by Formula 1:

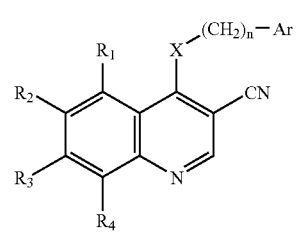

wherein:
Ar is a cycloalkyl of 3 to 7 carbon atoms, which may be optionally substituted with one or more alkyl of 1 to 6 carbon atoms, a pyridinyl, a pyrimidinyl, or a phenyl ring; wherein the pyridinyl, pyrimidinyl, or phenyl ring may be optionally mono-, di-, or tri-substituted with substituents selected from a group consisting of a halogen, an alkyl of 1-6 carbon atoms, an alkenyl of 2-6 carbon atoms, an alkynyl of 2-6 carbon atoms, azido, a hydroxyalkyl of 1-6 carbon atoms, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a benzoyl, an amino, an alkylamino of 1-6 carbon atoms, a dialkylamino of 2 to 12 carbon atoms, an alkanoylamino of 1-6 carbon atoms, an alkenoylamino of 3-8 carbon atoms, an alkynoylamino of 3-8 carbon atoms, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, a N,N-dialkylaminoalkyl of 3-10 carbon atoms, a N-alkylaminoalkoxy of 3-9 carbon atoms, a N,N-dialkylaminoalkoxy of 4-10 carbon atoms, mercapto, methylmercapto and benzoylamino;

a bicyclic aryl or bicyclic heteroaryl ring system of 8 to 12 atoms where the bicyclic heteroaryl ring contains 1 to 4 heteroatoms selected from N, O, and S, wherein the bicyclic aryl or bicyclic heteroaryl ring may be optionally mono- di-, tri, or tetra-substituted with a substituent comprising a halogen, an oxo, a thiocarbonyl, an alkyl of 1-6 carbon atoms, an alkenyl of 2-6 carbon atoms, an alkynyl of 2-6 carbon atoms, azido, a hydroxyalkyl of 1-6 carbon atoms, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, a N,N-dialkylaminoalkyl of 3-10 carbon atoms, an N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, and a benzoylamino;

a radical of the form:

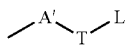

wherein;

A' is a pyridinyl, a pyrimidinyl, or a phenyl ring; wherein the pyridinyl, pyrimidinyl, or phenyl ring may be optionally mono- or di-substituted with a substituent comprising an alkyl of 1-6 carbon atoms, an alkenyl of 2-6 carbon atoms, an alkynyl of 2-6 carbon atoms, azido, a hydroxyalkyl of 1-6 carbon atoms, a halogen, a halomethyl, an alkoxymethyl of 2-7 carbon atoms, an alkoxy of 1-6 carbon atoms, an alkylthio of 1-6 carbon atoms, hydroxy, trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, a N-alkylaminoalkyl of 2-9 carbon atoms, a N,N-dialkylaminoalkyl of 3-10 carbon atoms, an N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, a alkenoyloxy of 3-8 carbon atoms, an alkynoyloxy of 3-8 carbon atoms, a carbamoyl, a N-alkylcarbamoyl of 2-7 carbon atoms, a N,N-dialkylcarbamoyl of 3-13 carbon atoms, and benzoylamino;

T is substituted at a carbon of the pyridinyl, pyrimidinyl, or phenyl ring with —NH(CH$_2$)$_m$—, —O(CH$_2$)$_m$—, —S(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S—, —SO(CH$_2$)$_m$—, —SO$_2$(CH$_2$)$_m$—, —CO(CH$_2$)$_m$—, —(CH$_2$)$_m$CO—, —(CH$_2$)$_m$SO—, —(CH$_2$)$_m$SO$_2$— or —(CH$_2$)$_m$NR—;

L is an imidazole or a phenyl ring wherein the imidazole or phenyl ring are optionally substituted at a carbon or nitrogen with one, two, or three substituents comprising an alkyl of 1-6 carbon atoms, an alkenyl of 2-6 carbon atoms, an alkynyl of 2-6 carbon atoms, azido, a hydroxyalkyl of 1-6 carbon atoms, a halogen, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, an N,N-dialkylaminoalkyl of 3-10 carbon atoms, a N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, a benzoylamino, a 5- or 6-membered heteroaryl ring where the heteroaryl ring contains 1 to 3 heteroatoms selected from N, O, and S and where the heteroaryl ring may be optionally mono- or di-substituted with a substituent comprising a halogen, an oxo, a thiocarbonyl, an alkyl of 1-6 carbon atoms, an alkenyl of 2-6 carbon atoms, an alkynyl of 2-6 carbon atoms, azido, a hydroxyalkyl of 1-6 carbon atoms, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, a N,N-dialkylaminoalkyl of 3-10 carbon atoms, a N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, and a benzoylamino;

m is 0-3;

n is 0-1;

X is NH, O, S, or NR;

R is alkyl of 1-6 carbon atoms;

$R_1$, $R_2$, $R_3$ and $R_4$ are a hydrogen, a halogen, a hydroxy, an amino, a hydroxyamino, a trifluoromethyl, a trifluoromethoxy, a mercapto, an alkyl of 1-6 carbon atoms, a cycloalkyl of 3-8 carbon atoms, an alkenyl of 2-6 carbon atoms, an alkynyl of 2-6 carbon atoms, an alkenyloxy of 2-6 carbon atoms, an alkynyloxy of 2-6 carbon atoms, a hydroxyalkyl of 1-6 carbon atoms, a mercaptoalkyl of 1-6 carbon atoms, a halomethyl, an alkoxymethyl of 2-7 carbon atoms, an alkoxy of 1-6 carbon atoms, a 2-methoxyethoxy, a 2-(2-methoxyethoxy)ethoxy, a cycloalkoxy of 3-8 carbon atoms, an alkylthio of 1-6 carbon atoms, a cycloalkylthio of 3-8 carbon atoms, an alkysulfinyl of 1-6 carbon atoms, an alkylsulfonyl of 1-6 carbon atoms, an alkylsulfonamido of 1-6 carbon atoms, an alkenylsulfonamido of 2-6 carbon atoms, an alkynylsulfonamido of 2-6 carbon atoms, an alkylcarboxamido of 2-7 carbon atoms, a (N-alkyl)alkylcarboxamido of 3-13 carbon atoms, an alkenylcarboxamido of 3-7 carbon atoms, an (N-alkyl)alkenylcarboxamido of 4-13 carbon atoms, an alkynylcarboxamido of 3-7 carbon atoms, an (N-alkyl)alkynylcarboxamido of 4-13 carbon atoms, cyano, nitro, carboxy, a alkoxycarbonyl of 2-7 carbon atoms, an alkanoyl of 2-7 carbon atoms, an alkenoyl of 3-7 carbon atoms, a N-alkyl-N-alkenylamino of 4 to 12 carbon atoms, an N,N-dialkenyamino of 6-12 carbon atoms, phenylamino, benzylamino, phenoxy, phenyl, thiophenoxy, benzyl, an alkylamino of 1-6 carbon atoms, an alkanoyloxy of 2-7 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, a dialkylamino of 2 to 12 carbon atoms, an alkanoyloxymethyl group of 2-7 carbon atoms, an alkenoyloxymethyl group of 2-7 carbon atoms, an alkynoyloxymethyl group of 2-7 carbon atoms, azido, benzoyl, a carboxyalkyl of 2-7 carbons, and a carboalkoxyalkyl of 3-8 carbon atoms,

—$NR_6C(O)H$; —$N(C(O)R_6)C(O)R_6$;

—Y—$(C(R_6)_2)_p$-Het1;

—Y—$(C(R_6)_2)_p$-Het1-$(C(R_6)_2)_q$-Z-$(C(R_6)_2)_r$-Het2;

Het1 is a 3-8 membered saturated heterocyclic ring containing one or more nitrogen, oxygen or sulfur atoms such as, but not limited to morpholine, thiomorpholine, thiomorpholine S-oxide, thiomorpholine S,S-dioxide, piperidine, pyrrolidine, aziridine, piperazine, tetrahydrothiophene, tetrahydrofuran, dioxane, 1,3-dioxolane pyrrole, tetrahydropyran, and diazepan; wherein Het1 is optionally mono- or di-substituted on a carbon or a nitrogen with $R_6$; optionally mono- or di-substituted on a carbon with hydroxy, —$N(R_6)_2$, or —$OR_6$; optionally mono or di-substituted on carbon with the mono-valent radicals —$(C(R_6)_2)_sOR_6$ or —$[(C(R_6)_2)_sN(R_6)_2]$; or optionally mono or di-substituted on a saturated carbon with divalent radicals =O or —$O(C(R_6)_2)_sO$—;

Het2 is a heteroaryl selected from the group comprising morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane pyrrole, and tetrahydropyran; wherein Het2 is optionally mono- or di-substituted on carbon or nitrogen with $R_6$; optionally mono- or di-substituted on carbon with hydroxy, —$N(R_6)_2$, or —$OR_6$; optionally mono or di-substituted on carbon with the mono-valent radicals —$(C(R_6)_2)_sOR_6$ or —$[(C(R_6)_2)_sN(R_6)2]$; or optionally mono or di-substituted on a saturated carbon with divalent radicals =O or —$O(C(R_6)_2)_sO$—;

$R_6$ is hydrogen, an alkyl of 1-6 carbon atoms, an alkenyl of 2-6 carbon atoms, an alkynyl of 2-6 carbon atoms, a cycloalkyl of 1-6 carbon atoms, an alkanoyl of 2-7 carbon atoms, a carbamoylalkyl of 2-7 carbon atoms, a hydroxyalkyl of 1-6 carbon atoms, a hydroxycycloalkyl of 3-6 carbon atoms, a carboxyalkyl of 2-7 carbon atoms, pyrrolidine, piperidine, or imidazole optionally substituted with methyl;

a phenyl optionally mono-, di-, or tri-substituted with halogen, an alkoxy of 1-6 carbon atoms, trifluoromethyl, amino, an alkylamino of 1-3 carbon atoms, a dialkylamino of 2-6 carbon atoms, nitro, cyano, azido, halomethyl, an alkoxymethyl of 2-7 carbon atoms, an alkanoyloxymethyl of 2-7 carbon atoms, an alkylthio of 1-6 carbon atoms, hydroxy, a carboxyl, a alkoxycarbonyl of 2-7 carbon atoms, phenoxy, phenyl, thiophenoxy, benzoyl, benzyl, phenylamino, benzylamino, an alkanoylamino of 1-6 carbon atoms or alkyl of 1-6 carbon atoms;

Y is O, S, —$NR_6C(O)$—, —$C(O)NR_6$—, $NR_6$ or a bond;

Z is O, S, —$NR_6C(O)$—, —$C(O)NR_6$—, $NR_6$ or a bond;

p is 0-4;

q is 0-4;

r is 0-4;

s is 1-6; and at least one of the groups, $R_1$, $R_2$, $R_3$ or $R_4$ is consisting of —Y—$(C(R_6)_2)_p$-Het1-$(C(R_6)_2)_q$-Z-$(C(R_6)_2)_r$-Het2;

X' is fluoro or chloro provided that when X' is chloro, $R_2$ is nitro;

G' is bromo, iodo, or sulfonate;

E is a leaving group or a sulfonate;

Q is a leaving group, aldehyde, and a ketone;

G is hydrogen, a halogen, hydroxy, amino, hydroxyamino, trifluoromethyl, trifluoromethoxy, mercapto, an alkyl of 1-6 carbon atoms, a cycloalkyl of 3-8 carbon atoms, an alkenyl of 2-6 carbon atoms, a alkynyl of 2-6 carbon atoms, a alkenyloxy of 2-6 carbon atoms, an alkynyloxy of 2-6 carbon atoms, a hydroxyalkyl of 1-6 carbon atoms, a mercaptoalkyl of 1-6 carbon atoms, halomethyl, an alkoxymethyl of 2-7 carbon atoms, an alkoxy of 1-6 carbon atoms, a 2-methoxyethoxy, a 2-(2-methoxyethoxy)ethoxy, a cycloalkoxy of 3-8 carbon atoms, an alkylthio of 1-6 carbon atoms, a cycloalkylthio of 3-8 carbon atoms, an alkysulfinyl of 1-6 carbon atoms, an alkylsulfonyl of 1-6 carbon atoms, an alkylsulfonamido of 1-6 carbon atoms, an alkenylsulfonamido of 2-6 carbon atoms, an alkynylsulfonamido of 2-6 carbon atoms, an alkylcarboxamido of 2-7 carbon atoms, a (N-alkyl)alkylcarboxamido of 3-13 carbon atoms, an alkenylcarboxamido of 3-7 carbon atoms, an (N-alkyl)alkenylcarboxamido of 4-13 carbon atoms, an alkynylcarboxamido of 3-7 carbon atoms, an (N-alkyl)alkynylcarboxamido of 4-13 carbon atoms, cyano, nitro, carboxy, a alkoxycarbonyl of 2-7 carbon atoms, an alkanoyl of 2-7 carbon atoms, an alkenoyl of 3-7 carbon atoms, a N-alkyl-N-alkenylamino of 4 to 12 carbon atoms, an N,N-dialkenylamino of 6-12 carbon atoms, phenylamino, benzylamino, phenoxy, phenyl, thiophenoxy, benzyl, an alkylamino of 1-6 carbon atoms, an alkanoyloxy of 2-7 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, a dialkylamino of 2 to 12 carbon atoms, an alkanoyloxymethyl group of 2-7 carbon atoms, an alkenoyloxymethyl group of 2-7 carbon atoms, an alkynoyloxymethyl group of 2-7 carbon atoms, azido, benzoyl, a carboxyalkyl of 2-7 carbons, a carboalkoxyalkyl of 3-8 carbon atoms, —$NR_6C(O)H$; —$N(C(O)R_6)C(O)R_6$; or a crystalline form or a pharmaceutically acceptable salt thereof.

Preferred compounds of the invention include the compounds of Formula 1 as follows:

4-({3-chloro-4-[(1-methyl-1H-imidazole-2-yl)thio]phenyl}amino)-6-methoxy-7-(4pyrrolidin-1-yl-piperidin-1-yl)quinoline-3-carbonitrile;

4-({3-chloro-4-[(1-methyl-1H-imidazole-2-yl)thio]phenyl}amino)-6-methoxy-7-(4-methylpiperazin-1-yl)quinoline-3-carbonitrile;

4-({3-chloro-4-[(1-methyl-1H-imidazole-2-yl)thio]phenyl}amino-6-methoxy-7-piperazin-1-yl)quinoline-3-carbonitrile;

6-methoxy-4-{[4-(2-methoxyphenoxy)phenyl]amino}-7-(4-pyrrolidin-1-ylpiperidin-1-yl)quinoline-3-carbonitrile, trifluoroacetate salt;

6-methoxy-4-[4-(pyridin-2-ylsulfanyl)-phenylamino]-7-(4-pyrrolidin-1-yl-piperidin-1-yl)-quinoline-3-carbonitrile;

4-[3-chloro-4-(pyridin-2-ylsulfanyl)-phenylamino]-6-methoxy-7-(4-pyrrolidin-1-yl-piperidin-1-yl)-quinoline-3-carbonitrile;

6-methoxy-4-[4-(pyridin-3-yloxy)-phenylamino]-7-(4-pyrrolidin-1-yl-piperidin-1-yl)-quinoline-3-carbonitrile;

4-({3-chloro-4-[(1-methyl-1H-imidazole-2-yl)thio]phenyl}amino)-7-(4-pyrrolidin-1-ylpiperidin-1yl)quinoline-3-carbonitrile;

4-({3-chloro-4-[(1-methyl-1H-imidazole-2-yl)thio]phenyl}amino)-6-(2-methoxyethoxy)-7-(4-pyrrolidin-1-ylpiperidin-1-yl))quinoline-3-carbonitrile;

4-({3-chloro-4-[(1-methyl-1H-imidazole-2-yl)thio]phenyl}amino)-6-ethoxy-7-(4pyrrolidin-1-ylpiperidin-1-yl)quinoline-3-carbonitrile;

7-(1,4'-bipiperidin-1'-yl)-4-({3-chloro-4-[(1-methyl-1H-imidazole-2-yl)thio]phenyl}amino)-6-methoxyquinoline-3-carbonitrile;

4-({3-chloro-4-[(1-methyl-1H-imidazole-2-yl)thio]phenyl}amino)-6-methoxy-7-[4-(4-methylpiperazin-1-yl)piperidin-1-yl]quinoline-3-carbonitrile;

4-({3-chloro-4-[(1-methyl-1H-imidazole-2-yl)thio]phenyl}amino)-6-methoxy-7-(4-morpholin-4-ylpiperidin-1-yl)quinoline-3-carbonitrile;

4-({3-chloro-4-[(1-methyl-1H-imidazole-2-yl)thio]phenyl}amino)-6-methoxy-7-[4-(1-methylpiperidin-4-yl)piperazin-1-yl]quinoline-3-carbonitrile;

4-({3-chloro-4-[(1-methyl-1H-imidazole-2-yl)thio]phenyl}amino)-7-( 4-[2-(1H-imidazole-1-yl)ethyl]piperazin-1-yl)-6-methoxyquinoline-3-carbonitrile;

6-Nitro-4-oxo-7-(4-pyrrolidin-1-ylpiperidin-1-yl)-1,4-dihydroquinoline-3-carbonitrile;

4-chloro-6-nitro-7-(4-pyrrolidin-1-ylpiperidin-1-yl)quinoline-3-carbonitrile;

4-({3-chloro-4-[(1-methyl-1H-imidazole-2-yl)thio]phenyl}amino)-6-nitro-7-(4-pyrrolidin-1-ylpiperidin-1-yl)quinoline-3-carbonitrile;

6-amino-4-[3-chloro-4-(1-methyl-1H-imidazole-2-ylsulfanyl)phenylamino]-7-(4-pyrrolidin-1-ylpiperidin-1-yl)quinoline-3-carbonitrile;

N-acetyl-N-[4-[3-chloro-4-(1-methyl-1H-imidazole-2-ylsulfanyl)-phenylamino]-3-cyano-7-(4-pyrrolidin-1-yl-piperidin-1-yl)quinoline-6-yl]acetamide;

N-[4-({3-chloro-4-[(1-methyl-1H-imidazole-2-yl)thio]phenyl}amino)-3-cyano-7-(4-pyrrolidin-1-ylpiperidin-1-yl)quinoline-6-yl]acetamide;

4-({3-chloro-4-[(1-methyl-1H-imidazole-2-yl)thio]phenyl}amino)-6-(methylamino)-7-(4-pyrrolidin-1-ylpiperidin-1-yl)quinoline-3-carbonitrile;

4-[(2,4-dichloro-5-methoxyphenyl)amino]-6-methoxy-7-(4-pyrrolidin-1-ylpiperidin-1-yl)quinoline-3-carbonitrile;

7-(2-[1,4']bipiperidinyl-1'-yl-ethoxy)-6-methoxy-4-(4-phenoxy-phenylamino)-quinoline-3-carbonitrile;

4-{3-chloro-4-[(1-methyl-1H-imidazole-2-yl)sulfanyl]anilino}-6-methoxy-7-{3-[4-(1-pyrrolidinyl)-1-piperidinyl]propoxy}-3-quinolinecarbonitrile;

4-(2,4-dichloro-5-methoxyanilino)-6-methoxy-7-[3-[4-(1-pyrrolidinyl)-1-7-]3-]4-(1-pyrrolidinyl)-1-piperidinyl]propoxy}-3-quinolinecarbonitrile;

4-{3-chloro-4-[(1-methyl-1H-imidazole-2-yl)sulfanyl]anilino}-6-methoxy-7-{2-[4-(1-pyrrolidinyl)-1-piperidinyl]ethoxy}-3-quinolinecarbonitrile;

6-methoxy-4-({4-[(1-methyl-1H-imidazole-2-yl)thio]phenyl}amino)-7-(4-pyrrolidin-1-ylpiperidin-1-yl)quinoline-3-carbonitrile; and 4-({3-chloro-4-[(1-methyl-1H-imidazole-2-yl)thio]phenyl}amino)-6-hydroxy-7-(4-pyrrolidin-1-ylpiperidin-1-yl)quinoline-3-carbonitrile.

In another embodiment this invention provides a method of inhibiting a Ras/Raf/MEK signaling cascade in a mammal comprising administering to the mammal an effective amount of a compound of Formula 1:

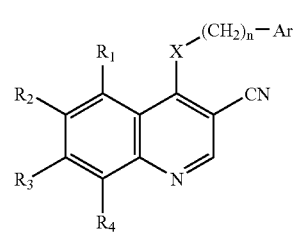

wherein the substitutions on the ring are previously described and includes a crystalline form or a pharmaceutically acceptable salt thereof.

In one embodiment the inhibition of the Ras/Raf/MEK signaling cascade prevents or inhibits stroke, osteoporosis, cancer, rheumatoid arthritis and inflammatory disease, polycystic kidney disease, and colonic polyps.

In a preferred embodiment the cancer is a melanoma, a pancreatic cancer, or a lung cancer.

In another embodiment the Ras/Raf/MEK signaling cascade in a mammal is inhibited by providing the mammal with an effective amount of at least one pharmaceutical composition, wherein the at least one pharmaceutical composition includes a compound of Formula 1:

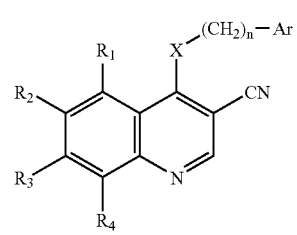

wherein the substitutions on the ring are previously described and includes a crystalline form or a pharmaceutically acceptable salt thereof.

In a preferred embodiment the mammal is provided with an effective amount of at least one biologically active agent provided prior to the at least one pharmaceutical composition, concurrently with the at least one pharmaceutical composition or after the at least one pharmaceutical composition.

An embodiment of this invention includes a means for preparing a compound of Formula I comprising:

a. reacting a compound of Formula 2

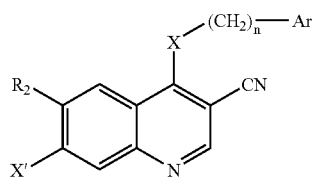

2 with a heated compound of Formula 3

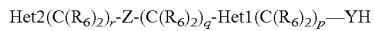

3 optionally with a base;

b. to yield the compound of Formula 1 having the structure

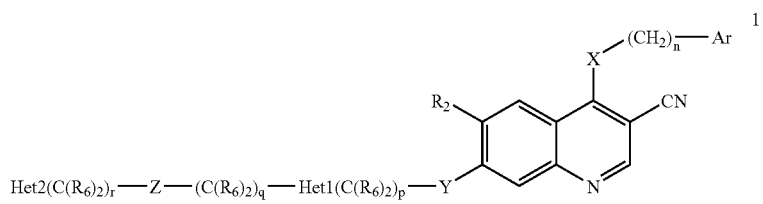

1 wherein the substitutions on the ring are previously described.

In another embodiment the invention includes a means for preparing a compound of Formula I comprising:

a. reacting a compound of Formula 2 or 7

2

7 with a heated compound of Formula 5

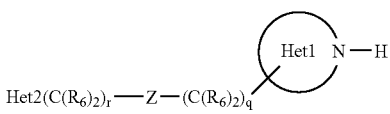

5 optionally with a base;

b. to yield the compound of Formula 1 having the structure

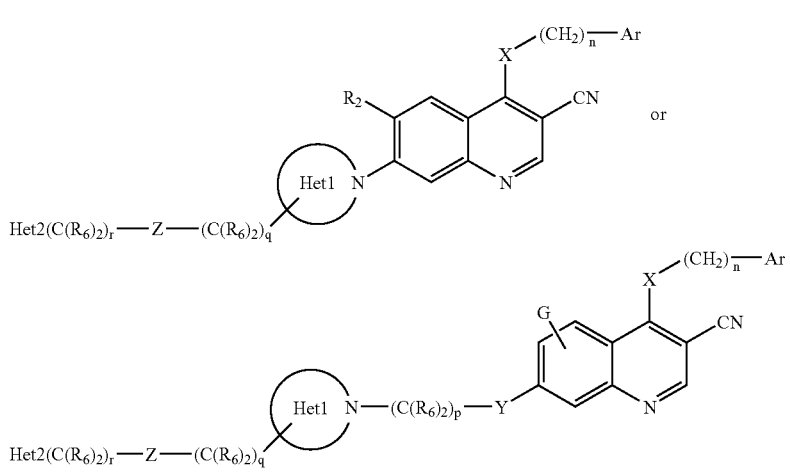

1 wherein the substitutions on the ring are previously described.

In another embodiment the invention describes a means for preparing a compound of Formula I comprising:

a. combining a compound of formula 9

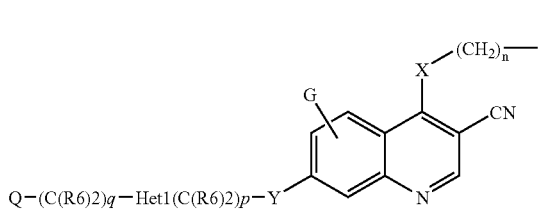

with a compound of Formula 10

Het2(C(R$_6$)$_2$)$_r$-ZH    10 to obtain a compound of Formula 1

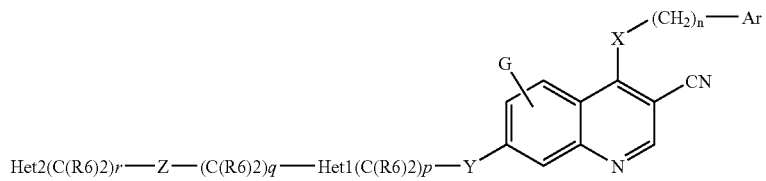

wherein the substitutions on the ring are previously described.

In an embodiment this invention includes a means for preparing a compound of Formula I comprising a. combining a compound of Formula 12 or 17

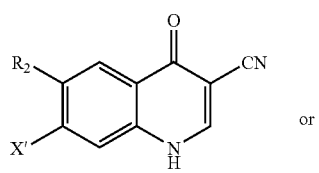

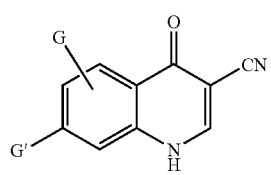

with a compound of Formula 3

Het2(C(R$_6$)$_2$)$_r$-Z-(C(R$_6$)$_2$)$_q$-Het1(C(R$_6$)$_2$)$_p$—YH    3 wherein, when G' is present a palladium catalyst is required to obtain a compound of Formula 13 or 18

13

Het2(C(R$_6$)$_2$)$_r$—Z—(C(R$_6$)$_2$)$_q$—Het1(C(R$_6$)$_2$)$_p$—Y—[quinolinone with R$_2$, O, CN]

or

18

Het2(C(R$_6$)$_2$)$_r$—Z—(C(R$_6$)$_2$)$_q$—Het1(C(R$_6$)$_2$)$_p$—Y—[quinolinone with G, O, CN]

b. combining the compound of Formula 13 or 18 with a halogenating agent in the presence of PO(Z)$_3$ to obtain a compound of Formula 14 or 19

14

Het2(C(R$_6$)$_2$)$_r$—Z—(C(R$_6$)$_2$)$_q$—Het1(C(R$_6$)$_2$)$_p$—Y—[quinoline with R$_2$, Z, CN]

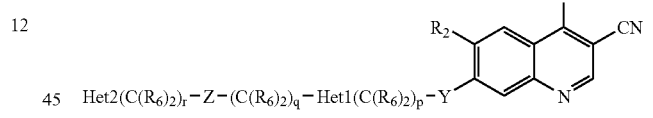

or

19

Het2(C(R$_6$)$_2$)$_r$—Z—(C(R$_6$)$_2$)$_q$—Het1(C(R$_6$)$_2$)$_p$—Y—[quinoline with G, Z, CN]

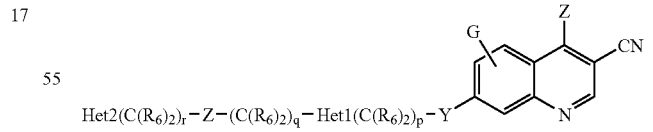

c. combining the compound of Formula 14 and 19 with a compound of Formula 15

15

$$\begin{array}{c} (CH_2)_n\text{—Ar} \\ HX \end{array}$$

to obtain a compound of Formula 1 or Formula 11

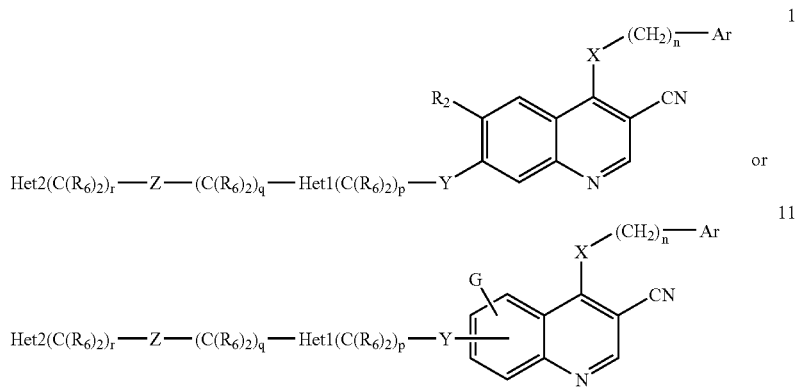

wherein the substitutions on the ring are previously described.

In another embodiment the invention includes a compound of Formula 12

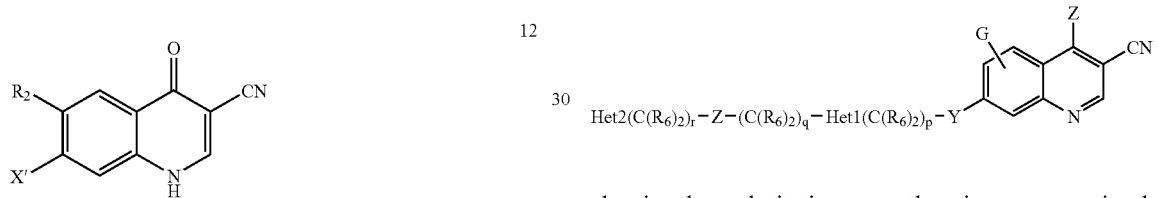

wherein the substitutions on the ring are previously described.

In another embodiment the invention includes a compound of Formula 13

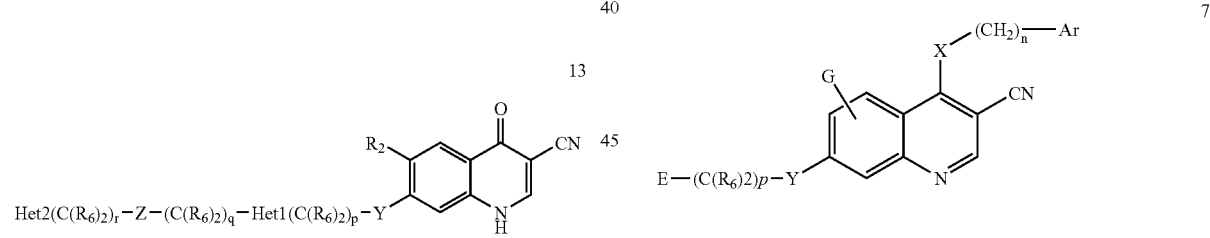

wherein the substitutions on the ring are previously described.

An embodiment the invention includes a compound of formula 18

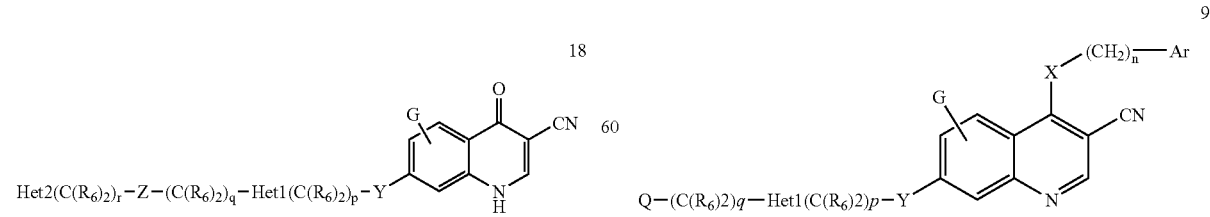

wherein the substitutions on the ring are previously described.

In an embodiment this invention includes a compound of Formula 19

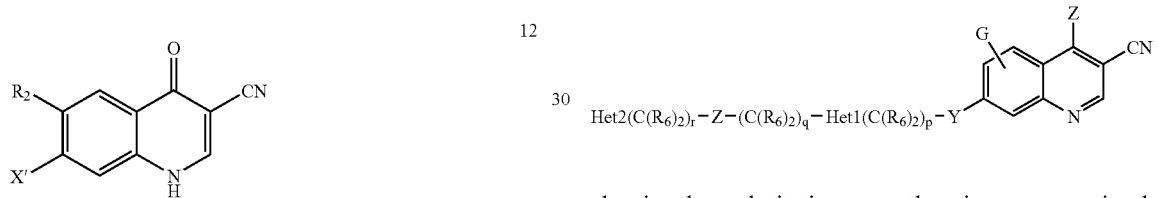

wherein the substitutions on the ring are previously described.

In an embodiment this invention includes a compound of Formula 7

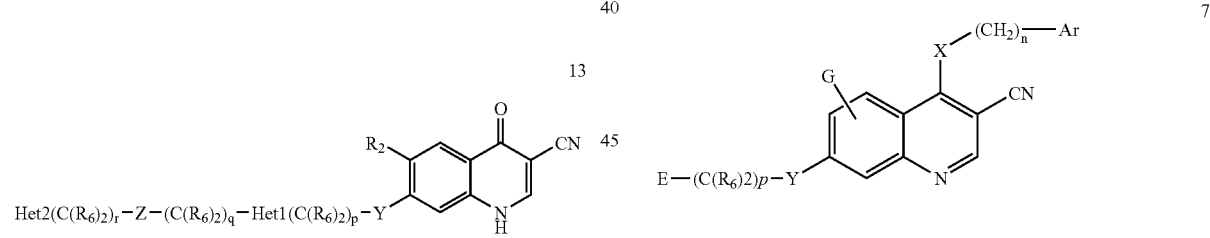

wherein the substitutions on the ring are previously described.

In another embodiment this invention includes a compound of formula 9

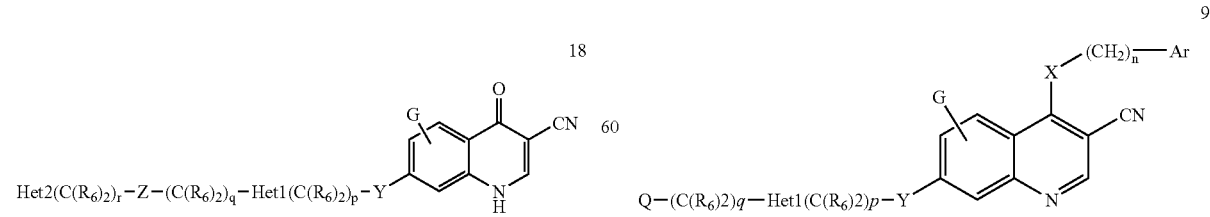

wherein the substitutions on the ring are previously described.

The following experimental details are set forth to aid in an understanding of the invention, and are not intended, and should not be construed, to limit in any way the invention set forth in the claims that follow thereafter.

DETAILED DESCRIPTION OF THE INVENTION

In accordance with this invention there is provided a group of compounds represented by Formula 1:

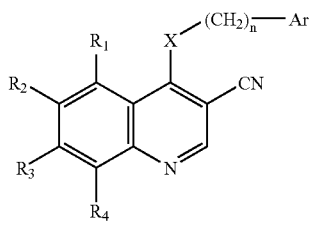

wherein the substitutions on the ring are previously described herein.

For purposes of this invention various terms are defined in the following paragraphs.

Alkanoyl is defined as a —COR" radical, where R" is an alkyl radical of 1-6 carbon atoms. Alkenoyl is defined as a —COR" radical, where R" is an alkenyl radical of 2-6 carbon atoms. Alkanoyloxy is defined as a —OCOR" radical, where R" is an alkyl radical of 1-6 carbon atoms. Alkanoyloxymethyl is defined as R"CO$_2$CH$_2$— radical, where R" is an alkyl radical of 1-6 carbon atoms.

The terms "alkenyl" and "alkynyl" refer to unsaturated aliphatic groups analogous in length and possible substitution to the alkyls described above, but which contain at least one double or triple carbon-carbon bond, respectively, in all possible configurational isomers, for example cis and trans. The alkenyl portion of the alkenyl, alkenyloxy, alkenylsulfonamido, substituents include both straight chain as well as branched carbon chains and one or more sites of unsaturation and all possible configurational isomers.

The term "alkoxy" as used herein refers to an alkyl group, as defined above, having an oxygen radical attached thereto. Representative alkoxyl groups include methoxy, ethoxy, propyloxy, tert-butoxy and the like. The term alkoxy can be used alone or as part of a chemical name as in for example, "alkoxy-enaminonitrile". The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. Alkoxycarbonyl of 2-7 carbon atoms is defined as a —CO$_2$R" radical, where R" is an alkyl radical of 1-6 carbon atoms.

Alkoxymethyl is defined as R"OCH$_2$ radical where R" is an alkyl radical of 1-6 carbon atoms.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In a preferred embodiment, a straight chain or branched chain alkyl has 6 or fewer carbon atoms in its backbone. The term "alkyl" can be used alone or as part of a chemical name as in for example, alkoxy, alkanoyloxy, alkoxymethyl, alkanoyloxymethyl, alkysulfinyl, alkylsulfonyl, alkylsulfonamido, alkoxycarbonyl, alkynyloxy, alkanoylamino, N-alkylcarbamoyl, N,N-dialkylcarbamoyl , N-alkylaminoalkoxy, N-alkyl-amino-alkyl, N,N-dialkylaminoalkyl, hydroxyalkyl, alkylthio, and N,N-dialkylaminoalkoxy include both straight chain as well as branched carbon chains.

Alkylcarboxamido, alkenylcarboxamido, alkynylcarboxamido are defined as R"CONH— radical, where R" is an alkyl radical of 1-6 carbon atoms, an alkenyl radical of 2-6 carbon atoms, or an alkynyl radical of 2-6 carbon atoms, respectively. (N-alkyl)alkenylcarboxamido, alkynylcarboxamido, (N-alkyl)alkynylcarboxamido are defined as R"CO(R')N— radical, where R' is an alkyl radical of 1-6 carbon atoms, R" is an alkyl radical of 1-6 carbon atoms, an alkenyl radical of 2-6 carbon atoms, or an alkynyl radical of 2-6 carbon atoms, respectively. N-alkylcarbamoyl is defined as R"NHCO— radical, where R" is an alkyl radical of 1-6 carbon atoms. N,N-dialkylcarbamoyl is defined as R"R'NCO— radical, where R" is an alkyl radical of 1-6 carbon atoms, R' is an alkyl radical of 1-6 carbon atoms and R' and R" may be the same or different.

Alkysulfinyl is defined as R"SO— radical, where R" is an alkyl radical of 1-6 carbon atoms. Alkylsulfonyl is defined as R"SO$_2$— radical, where R" is an alkyl radical of 1-6 carbon atoms. Alkylsulfonamido, alkenylsulfonamido, alkynylsulfonamido are defined as R"SO$_2$NH— radical, where R" is an alkyl radical of 1-6 carbon atoms, an alkenyl radical of 2-6 carbon atoms, or an alkynyl radical of 2-6 carbon atoms, respectively.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—. Representative alkylthio groups include methylthio, ethylthio, and the like.

The terms "amine", "amino", and "amide" are art recognized and refer to both unsubstituted and substituted amines. The terms can be used in combination with other terms described herein, for example, alkylamino, aminoalkyl, dialkylamino, alkanoylamino, and alkenoylamino.

The term "aryl" as used herein includes 4-, 5-, 6-, 7- and 10-membered single ring or fused multiple rings aromatic groups, which may substituted or unsubstituted. For purposes of this invention the term "aryl" is defined as an aromatic carbocyclic moiety and may be substituted or unsubstituted. Preferred aryl groups have 6 to 14 carbon atoms. Particularly preferred aryl groups are phenyl and napthyl. The aromatic ring can be optionally independently mono-, di-, tri- or tetra-substituted. Preferred substituents are selected from the group consisting of, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties and —CN. The term "aryl" also includes polycyclic ring systems having two or more rings in which two or more carbons are common to two adjoining rings (the rings are "fused") wherein at least one of the carbocyclic rings is aromatic, e.g., the other rings can be cycloalkyls, cycloalkenyls, cycloalkynyls, and/or aryls.

The term azido represents a compound that includes a group N:N.N—.

For purposes of this invention a base could be, but is not limited to, triethylamine, Huenig's base (diisopropylethylamine), or an inorganic base such as potassium carbonate.

Benzoyl is a term that represents a benzene with a carbonyl with the attachment at the carbonyl. Such term can be used alone or in combination with terms previously describe, as for example, benzoylamino.

The term carbamoyl represents the radical NH$_2$CO— from carbamic acid.

The term carbonyl represents the radical =CO.

Carboxy is defined as a —CO$_2$H radical. Carboxyalkyl is defined as a HO$_2$C—R'"— radical where R'" is a divalent alkyl radical of 1-6 carbon atoms. Carboalkoxyalkyl is defined as a R"O$_2$C—R'"— radical where R'" is a divalent alkyl radical and where R" and R'" may be the same or different, and together have 2-7 carbon atoms.

Cyano represents the radical NC—.

The cycloalkyl portions of cycloalkyl, N-cycloalkylamino, N-cycloalkyl-N alkylaminoalkyl, N,N-dicycloalkylaminoalkyl, cycloalkylthio and azacycloalkyl substituents include both simple carbocycles as well as carbocycles containing alkyl substituents, where a carbocycle is a cyclic compound where all the ring members are carbon.

The compounds of this invention may contain one or more asymmetric carbons atoms; in such cases, the compounds of this invention include the individual diasteromers, the racemates, and the individual R and S entantiomers thereof. Some of the compounds of this invention may contain one or more double bonds; in such cases, the compounds of this invention include each of the possible configurational isomers as well as mixtures of these isomers. The compounds of this invention may contain an asymmetric carbon atom and some of the compounds of this invention may contain one or more asymmetric centers and may thus give rise to stereoisomers, such as enantiomers and diastereomers. The stereioisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

The term "halogen" refers to an atom of fluorine, chlorine, bromine, or iodine. A halogen can be combined with halogens or other groups, as for example in the case of, halomethyl or trifluoromethyl.

The term "heteroaryl" refers to a 3 to 8 membered ring structure, which ring structure includes one to four heteroatoms. Heteroaryls include, but are not limited to, pyrrolidine, oxolane, thiolane, piperidine, piperazine, pyrrole, furan, thiophene, imidazole, oxazole, thiazole, triazole, pyrazole, pyridine, pyrazine, pyridazine and pyrimidine, and morpholine. For purposes of this invention a heteroaryl comprises a heterocyclic ring system of one to three fused rings and contains 1 to 4 heteroatoms the same or different selected from the group consisting of S, N, and O. The remaining rings of the ring system may be fully unsaturated, partially saturated, or fully saturated. Each ring comprises three to ten members. Preferred heteroaryl groups are thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, pteridine, carbazole, phenanthridine, acridine, perimidine, phenanthroline, phenazine, phenothiazine, furazan, phenoxazineand pyrrolidine. The heteroaryl can be independently substituted at one or more positions. Preferred substituents are halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, acyl, aldehyde, ester, a cycloheteroalkyl, an aromatic or heteroaromatic moiety, —CN, or Y. When the heteroaryl is substituted with Y, wherein Y is —NH, —O—, —S—, or —NR—, wherein R is an alkyl of 1-6 carbon atoms, at one position on the ring there is further substitution on the —NH, —O—, —S—, or —NR— with a (CH$_2$)n-X group. For purposes of this invention n is 0-1 and "X" is cycloalkyl of 3 to 7 carbon atoms, which may be optionally substituted with one or more alkyl of 1 to 6 carbon atoms; or is a pyridinyl, pyrimidinyl, or phenyl ring; wherein the pyridinyl, pyrimidinyl, or phenyl ring may be optionally mono- di-, or tri-substituted with substituents independently selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, benzoylamino, and -Q-(CH$_2$)$_m$Ar, wherein Q is selected from O, NH, N(C$_1$-C$_6$ alkyl) or S, m is 0, 1 or 2, and Ar is phenyl or pyridyl optionally substituted with one to three moieties independently selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms and benzoylamino.

It is understood by one skilled in the art that the heteroaryl or bicyclic heteroaryl Ar groups of the compounds of Formula I do not contain O—O, S—S, or S—O bonds, as they would be unstable. Preferred bicyclic aryl or bicyclic heteroaryl ring systems include naphthalene, tetralin, indan, 1-indanone, 1,2,3,4-tetrahydroquinoline, naphthyridine, benzofuran, 3-oxo-1,3-dihydroisobenzofuran, benzothiophene, 1,1-dioxo-benzothiophene, indole, indoline 1,3-dioxo-2,3-dihydro-1H-isoindole, benzotriazole, 1H-indazole, indoline, indazole, 1,3-benzodioxole, benzoxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydrobenzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydrophthalazine, 2-oxo-1,2-dihydroquinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings are pyridine, pyrimidine, imidazole, thiazole, thiazolidine, pyrrole, furan, thiophene, oxazole, or 1,2,4-triazole.

Either or both rings of the bicyclic aryl or bicyclic heteroaryl Ar group may be fully unsaturated, partially saturated, or fully saturated. An oxo substituent on the bicyclic aryl or bicyclic heteroaryl moiety means that one of the carbon atoms has a carbonyl group. A thiocarbonyl substituent on the bicyclic aryl or bicyclic heteroaryl moiety means that one of the carbon atoms has a thiocarbonyl group.

When L is a 5 or 6-membered heteroaryl ring, it may be fully unsaturated or partially saturated. The heteroaryl ring can be bound to A' via carbon or nitrogen.

The term "heteroatom" as used herein means an atom of any element other than carbon or hydrogen. Preferred heteroatoms are nitrogen, oxygen, sulfur, phosporus, and selenium. The term "heteroatom" as used herein means an atom of any element other than carbon or hydrogen. Preferred heteroatoms are nitrogen, oxygen, sulfur and phosphorous.

Mercapto is a prefix or suffix representing a thio group —SH, for example, methylmercapto.

As used herein, the term "nitro" means $-NO_2$.; the term "halogen" designates —F, —Cl, —Br or —I; the term "sulfhydryl" means —SH; the term "hydroxyl" means —OH; and the term "sulfonyl" means —SO—.

The term phenoxy represents the radical PhO, a form of phenol. A phenol is an aryl hydroxide. Both terms can be used alone or in conjunction with terms described herein, such as, thiophenoxy or phenylamino.

The term oxo is a prefix indicating the keto group, as for example oxomalonic acid, HOOC—CO—COOH.

The pharmaceutically acceptable salts are those derived from such organic and inorganic acids such as: acetic, lactic, citric, tartaric, succinic, maleic, malonic, gluconic, hydrochloric, hydrobromic, phosphoric, nitric, sulfuric, methanesulfonic, and similarly known acceptable acids.

As used herein, the term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The compounds of this invention when part of a pharmaceutical composition, may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules. When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of this invention when part of a pharmaceutical composition, of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The compounds of this invention may be provided orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 300 mg of a compound of the invention and preferably from 2 to 100 mg. Still further preferred unit dosage forms contain 5 to 50 mg of a compound of the present invention. The compounds of the present invention can be administered orally at a dose range of about 0.01 to 100 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer. The compound of the present invention may be delivered locally via a capsule that allows a sustained release of the compound over a period of time. Controlled or sustained release compositions include formulation in lipophilic depots (for example, fatty acids, waxes, oils).

The dose provided to a patient will vary depending upon what is being provided, the purpose of providing, the manner of providing, and the like. A "therapeutically effective amount" is an amount sufficient to inhibit an Ras/Raf/MEK signaling cascade in a mammal comprising. The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

For purposes of this invention a "neoplasm" is defined as cells selected from the breast, kidney, bladder, mouth, larynx, esophagus, stomach, colon, ovary, pancreas, brain, prostrate and lung having a morphology not found in the majority of the cells of a mammal.

As used in accordance with this invention, the term providing an effective amount of a compound means either directly administering such compound, or administering a prodrug, derivative, or analog which will form an effective amount of the compound within the body.

In one embodiment, the present invention provides for a method of inhibiting the neoplasm. The method comprises contacting a cell with an amount of a compound effective to decrease or prevent Ras/Raf/MEK signaling cascade function. The cell may be a mammalian cell and more specifically a human cell. The cell may also be a bacterial cell such as for example *E coli*. The cell may include but is not limited to a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

In another embodiment, the present invention provides a method for the treatment or prevention of a neoplasm in a mammal. The present invention accordingly provides to a mammal, a pharmaceutical composition that comprises a compound of this invention in combination or association with a pharmaceutically acceptable carrier. The compound of this invention may be administered alone or in combination with other therapeutically effective compounds or therapies for the treatment or prevention of the neoplasm.

The present invention further provides a compound of the invention for use as an active therapeutic substance for preventing neoplasm.

The present invention further provides a method of treating neoplasm in humans, which comprises administering to the infected individual an effective amount of a compound or a pharmaceutical composition of the invention.

The present invention provides a method of inhibiting Ras/Raf/MEK signaling cascade. The method comprises contacting a cell with an amount of a compound effective to decrease or prevent the Ras/Raf/MEK signaling cascade. The cell may be a mammalian cell and more specifically a human cell. The cell may be a normal cell, an activated cell, a neoplastic cell, a diseased cell, or an infected cell. The cell is not limited to a cell type.

As used herein the at least one biologically active agent is selected from the group consisting of interferon, a pegylated interferon, a ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

The preparation of the compounds and intermediates of this invention encompassed by Formula 1 is described below in Flowsheet 1 wherein Ar, X, n, p, q, r, $R_2$, $R_6$, Z, Het1 and Het2 are herein before defined. Y is O, S or $NR_6$.

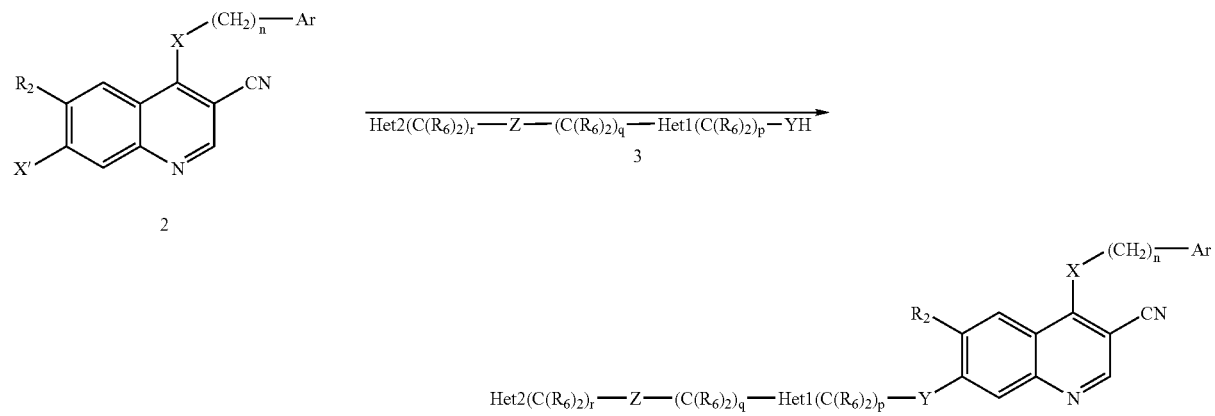

Intermediates 2, wherein Ar, X, n and $R_2$ are herein before defined, and X' is fluoro or chloro (with the proviso that when X' is chloro, $R_2$ is nitro) can be prepared by methods outlined in U.S. Pat. Nos. 6,002,008, 6,288,082, and 6,297,258, hereby incorporated by reference. Intermediates 3, wherein p, q, r, $R_6$, Z, Het1 and Het2 are herein before defined, and Y is O, S or $NR_6$, are commercially available, or can be prepared by methods in the chemistry literature by a chemist skilled in the art. Displacement of the flourine atom of compounds of Formula 2 at C-7 can be carried out by heating with compounds of Formula 3, in the presence or absence of added base to provide target compounds of Formula 1.

The preparation of compounds of Formula 6 can be carried out as outlined in Flowsheet 2. Nucleophile 5, wherein Het1 possesses a reactive NH moiety, q, r, $R_6$, Z and Het2 are herein before defined, can be reacted with intermediate 2, wherein Ar, X, X', n and $R_2$ are herein before defined, at elevated temperatures, with or without added base to provide compounds of Formula 6.

Flowsheet 2

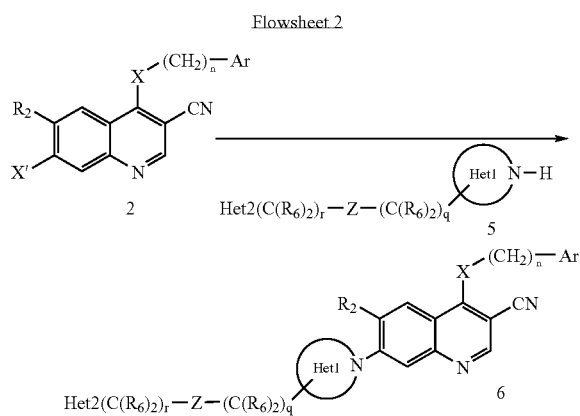

The preparation of compounds of Formula 20 can be carried out as outlined in Flowsheet 3. Compounds of Formula 7, wherein Ar, X, n, p, $R_6$ are herein before defined, E is a leaving group such as, but not restricted to halo, tosylate, mesylate, Y is O, G is $R_1$, $R_2$ or $R_4$, some of which can be prepared as described in U.S. Pat. Nos. 6,288,082 and 6,297,258, hereby incorporated by reference. Nucleophile 5, wherein Het1 possesses a reactive NH moiety, q, r, $R_6$, Z and Het2 are herein before defined, can be reacted with intermediate 7 to provide compounds of Formula 6 using chemistry methodology described in U.S. Pat. Nos. 6,288,082 and 6,297,258, hereby incorporated by reference.

Flowsheet 3

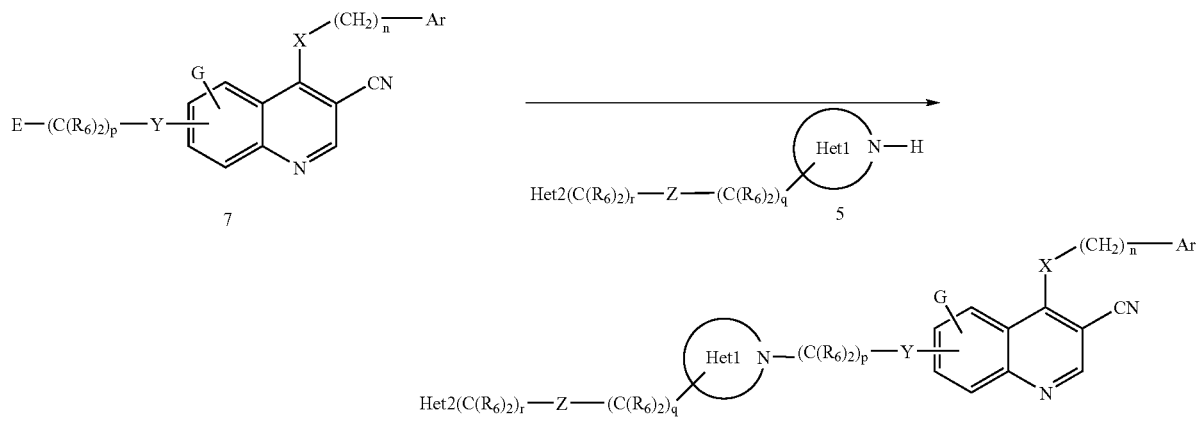

The preparation of the compounds and intermediates of this invention encompassed by Formula 11 can also be carried out by methods outlined in Flowsheet 4 wherein Ar, X, n, p, q, r, $R_6$, Z, Y, G, Het1 and Het2 are herein before defined.

Flowsheet 4

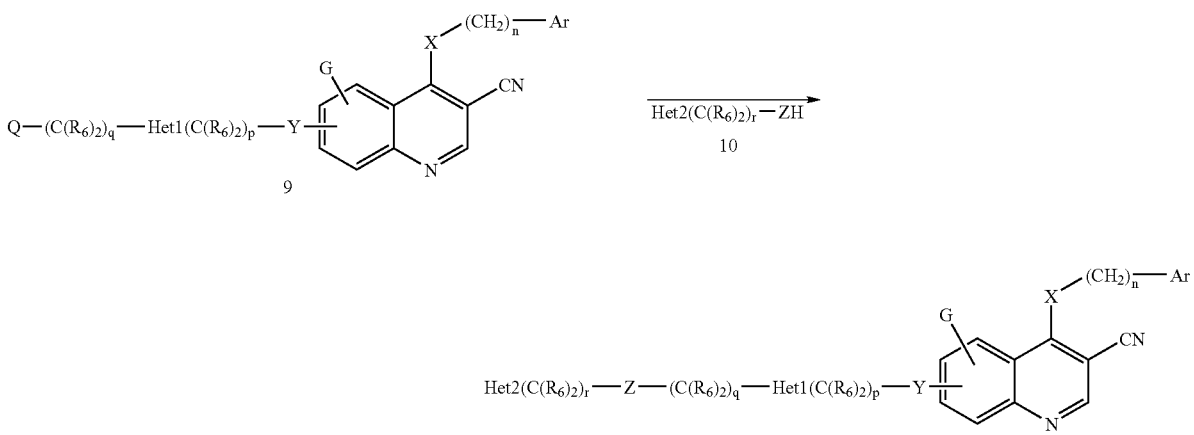

Intermediates 9, wherein Ar, X, Y, Het1, $R_6$, p, q, n and G are herein before defined, Q is a leaving group such as halo, triflate, mesylate, tosylate, or alternatively, an alcohol, aldehyde or ketone, can be prepared by methods outlined in U.S. Pat. Nos. 6,002,008, 6,288,082, and 6,297,258, hereby incorporated by reference. Intermediates 10, wherein r, $R_6$, and Het2 are herein before defined, Z is O, S or $NR_6$, are commercially available, or can be prepared by methods in the chemistry literature by a chemist skilled in the art. Alternatively, Z is a bond, r=0 Het2 possesses a nucleophilic nitrogen atom. The reaction of compounds of Formula 10 with compounds of Formula 9 can be carried out to provide target compounds 11 by a variety of methodologies, including: nucleophilic displacement of a leaving group, reductive amination or coupling in the presence of reagents such as diethylazodicarboxylate and triphenylphosphine and other methods known to chemists skilled in the art.

The preparation of the compounds and intermediates of this invention encompassed by Formula 4 is described below in Flowsheet 5 wherein Ar, X, n, p, q, r, $R_2$, $R_6$, Z, Het1 and Het2 are herein before defined. Y is O, S or $NR_6$.

Compounds of Formula 12 where $R_2$ and X' are hereinbefore defined, can be prepared as described in US 2001051620, hereby incorporated by reference. The reaction of 7-substituted-4-oxo-1,4-dihydro-3-quinolinecarbonitriles 12 with intermediates 3, wherein p, q, r, $R_6$, Z, Het1 and Het2 are herein before defined, and Y is O, S or $NR_6$, provides compounds of Formula 13. Alternatively, Y is a bond, p=0 and Het1 possesses a nucleophilic nitrogen atom. Treatment of 7-substituted-4-oxo-1,4-dihydro-3-quinolinecarbonitriles 13 with a halogenating reagent $PO(Z)_3$ wherein Z is a chloro or bromo group which include but not limited to phosphorous oxychloride, phosphorous oxybromide either neat or optionally in the presence of a cosolvent which include but not limited to dichloromethane affords 7-substituted-4-halo-3-quinolinecarbonitriles 14. Compounds of Formula 14 are further reacted with a nucleophile of Formula 15 wherein Ar, n and X are as hereinbefore defined, in a solvent such as 2-ethoxyethanol in the presence of a catalytic or equivalent amount of pyridine hydrochloride, or by using bases such as trialkylamines, sodium hydride in an inert solvent, sodium or Flowsheet 5

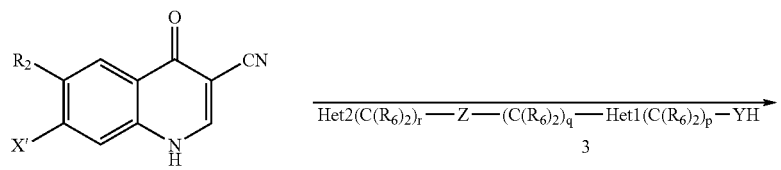

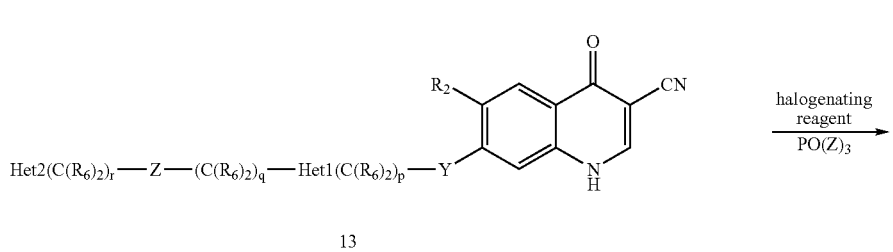

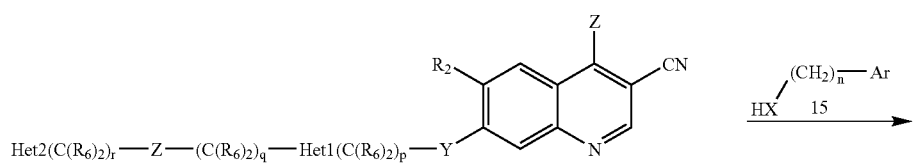

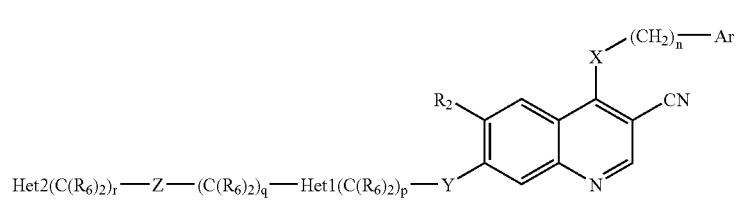

potassium alkoxides in an alcohol solvents, and the like to provide products of Formula 1.

The preparation of the compounds and intermediates of this invention encompassed by Formula 11 is described below in Flowsheet 6 wherein Ar, X, n, p, q, r, $R_6$, Z, Het1 and Het2 are herein before defined. G is $R_1$, $R_2$, $R_3$ or $R_4$. Y is O or $NR_6$.

commercially available, or can be prepared by methods in the chemistry literature by a chemist skilled in the art. The reaction of compounds of Formula 3 with intermediates 16 can be carried out with an appropriately substituted palladium catalyst, in the presence of certain ligands (Muci, Alex R.; Buchwald, Stephen L. Practical palladium catalysts for C—N and

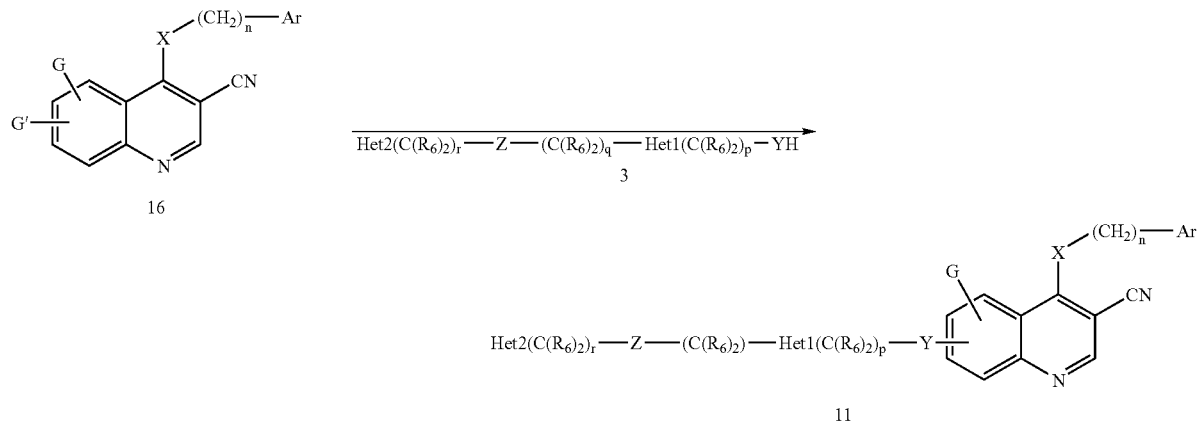

Flowsheet 6

Intermediates 16, wherein Ar, X and n are herein before defined, G is $R_1$, $R_2$, $R_3$ or $R_4$ and G' is bromo, iodo or a sulfonate such as, but not restricted to trifluoromethanesulfonate, can be prepared by methods outlined in U.S. Pat. Nos. 6,002,008, 6,288,082, and 6,297,258, hereby incorporated by reference. Intermediates 3, wherein p, q, r, $R_6$, Z, Het1 and Het2 are herein before defined, and Y is O, S or $NR_6$, p=0 and Het1 possesses a nucleophilic nitrogen atom, are C—O bond formation. *Topics in Current Chemistry* 2002, 219, 131-209) to provide target compounds 11. Alternatively, Y is a bond, p=0 and Het1 possesses a nucleophilic nitrogen atom.

The preparation of the compounds and intermediates of this invention encompassed by Formula 11 is described below in Flowsheet 7 wherein Ar, X, n, p, q, r, $R_6$, Z, Het1 and Het2 are herein before defined. G is $R_1$, $R_2$, $R_3$ or $R_4$. Y is O or $NR_6$.

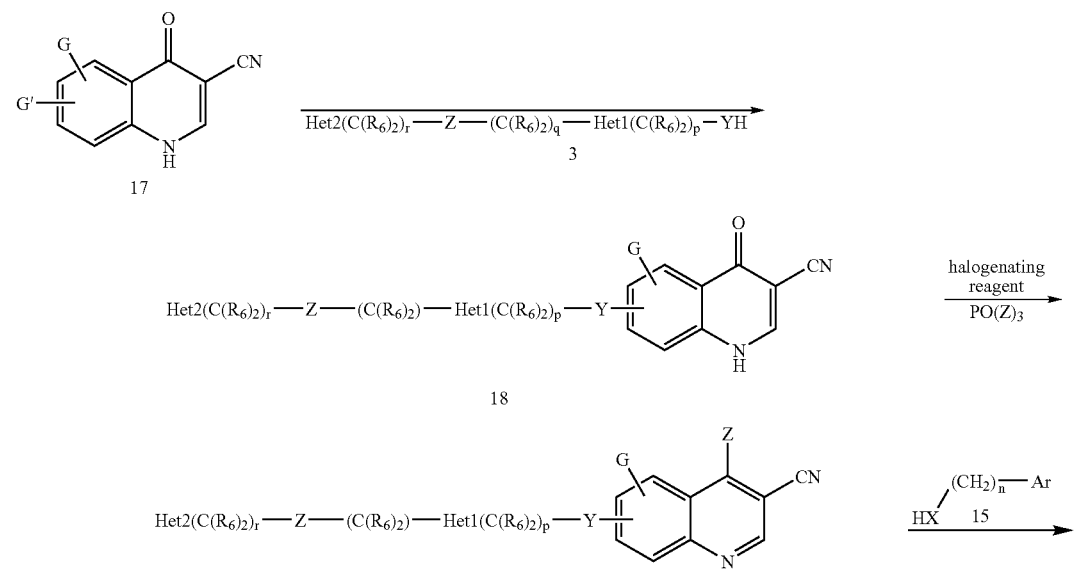

Flowsheet 7

-continued

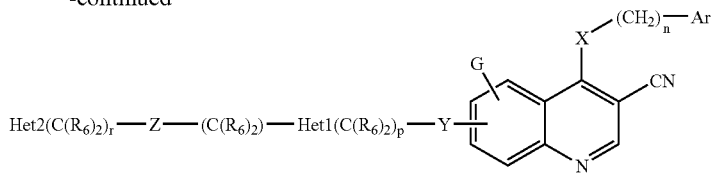

11

Compounds of Formula 17 where G is $R_1$, $R_2$, $R_3$ or $R_4$ and G' is bromo, iodo or a sulfonate such as, but not restricted to trifluoromethanesulfonate, can be prepared by methods outlined in U.S. Pat. Nos. 6,002,008, 6,288,082, and 6,297,258, hereby incorporated by reference. The reaction of 7-substituted-4-oxo-1,4-dihydro-3-quinolinecarbonitriles 17 with intermediates 3, wherein p, q, r, $R_6$, Z, Het1 and Het2 are herein before defined, and Y is O or $NR_6$, or Y is a bond, p=0 and Het1 possesses a nucleophilic nitrogen atom, provides compounds of Formula 18 when coupled with literature methods (Muci, Alex R.; Buchwald, 10 Stephen L. Practical palladium catalysts for C—N and C—O bond formation. *Topics in Current Chemistry* 2002, 219, 131-209). Treatment of 7-substituted-4-oxo-1,4-dihydro-3-quinolinecarbonitriles 18 with a halogenating reagent $PO(Z)_3$ wherein Z is a chloro or bromo group which include but not limited to phosphorous oxychloride, phosphorous oxybromide either neat or optionally in the presence of a cosolvent which include but not limited to dichloromethane affords 7-substituted-4-halo-3-quinolinecarbonitriles 19. Compounds of Formula 19 are further reacted with a nucleophile of Formula 15 wherein Ar, n and X are as hereinbefore defined, in a solvent such as 2-ethoxyethanol in the presence of a catalytic or equivalent amount of pyridine hydrochloride, or by using bases such as trialkylamines, sodium hydride in an inert solvent, sodium or potassium alkoxides in an alcohol solvents, and the like to provide products of Formula 11.

In those cases where the Ar, G, $R_1$, $R_2$, $R_3$ and $R_4$ substituents may contain an asymmetric carbon atom, the intermediates can be used as the racemate or as the individual R or S enantiomers in which case the compounds of this invention will be in the racemic or R and S optically active forms, respectively. In cases where the substituents may contain more than one asymmetric carbon atoms, diastereomers may be present; these can be separated by methods well known in the art including, but not limited to, fractional crystallization and chromatographic methods.

Converting the $R_2$ groups of Formula 2, 4, 6, 12, 13 and 14 to different $R_2$ groups, or converting the G groups of Formula 7, 8, 9 and 11, 16, 17, 18 and 19 to various $R_1$, $R_2$, $R_3$ and $R_4$ groups can be accomplished through any conventionally known techniques.

Representative compounds of this invention are evaluated in several standard pharmacological test procedures that showed that the compounds of this invention possess significant activity as inhibitors of Ras/Raf/MAPK cascade and are antiproliferative agents. Disease states which can be treated or inhibited by protein kinase inhibitors include those in which the etiology is at least in part caused by a defect upstream in a signaling pathway from a protein kinase (i.e., colon cancer); those in which the etiology is at least in part caused by an overexpressed protein kinase (i.e., lung cancer and colonic polyps); and those in which the etiology is at least in part caused by a dysregulated protein kinase (gene turned on at all times; glioblastoma).

Based on the activity shown in the standard pharmacological test procedures, the compounds of this invention are therefore useful as antineoplastic agents.

The test procedures used and results obtained are shown below.

Mitogen Activated Protein Kinase (MAPK) Test Procedure

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, is used. Recombinant human MEK 1 (MAPKK) is first used to activate recombinant human ERK2 (MAPK) and the activated MAPK (ERK) is incubated with substrate (myelin basic protein peptide (MBPP) or Myc peptide) in the presence of ATP, $Mg^{+2}$ and radiolabeled $^{33}P$ ATP. The phosphorylated peptide is captured on a P 81 phosphocellulose filter (paper filter or embedded in microtiter plate) ished and counted by scintillation methods.

The peptide substrates used in the assay are MBPP, peptide substrate (APRTPGGRR), or synthetic Myc substrate, (KKFELLPTPPLSPSRR.5 TFA). The recombinant enzymes used are prepared as GST fusion proteins of human ERK 2 and human MEK 1. Inhibitor samples are prepared as 10× stocks in 10% DMSO and an appropriate aliquot is used to deliver either 10 ug/ml for a single point screening dose or 100 to 0.0001 uM final concentration for a dose response curve. Final DMSO concentrations are less than or equal to 1%.

The reaction is run as follows in 50 mM Tris kinase buffer, pH 7.4 in a reaction volume of 50 ul. The appropriate volume of kinase buffer and inhibitor sample is added to the tube. Appropriate dilution of enzyme is delivered to give 2-5 µg recombinant MAPK (Erk) per tube. The inhibitor is incubated with MAPK (Erk) for 30 minutes at 0° C. Recombinant Mek (MAPKK) (0.5-2.5 ug) or fully activated Mek (0.05-0.1 units) is added to activate the Erk and incubated for 30 minutes at 30° C. Then substrate and $^{33}P$ ATP are added to give a final concentration of 0.5-1 mM MBPP or 250-500 µM Myc; 0.2-0.5 µCi gamma P 33 ATP/tube; 50 µM ATP final concentration. Samples are incubated at 30° C. for 30 minutes and the reaction is stopped by adding 25 µl of ice cold 10% trichloroacetic acid (TCA). After samples are chilled on ice for 30 minutes, 20 µl of sample is transferred onto P 81 phosphocellulose filter. Filter papers are washed 2 times with a large volume of 1% acetic acid, then 2 times with water. The filters are briefly air dried before addition of scintillant and samples are counted in the appropriate scintillation counter set up for reading $^{33}P$ isotope. Samples included a positive control (activated enzyme plus substrate); a no enzyme control; a no substrate control; samples with different concentrations of putative inhibitor; and samples with reference inhibitors (other active compounds or non-specific inhibitors such as staurosporine or K252 B).

The raw data is captured as counts per minute (cpm). Sample replicates are averaged and corrected for background count. Mean cpm data is tabulated by group and % inhibition by a test compound is calculated as (corrected cpm control-corrected. cpm sample/control)×100=% inhibition). If several concentrations of inhibitor are tested, $IC_{50}$ values (the concentration which gives 50% inhibition) are determined graphically. The results obtained for representative compounds of this invention are listed in Table 1.

Src Kinase Test Procedrue

Inhibitors of $p60^{c-src}$ (partially purified preparation purchased from Upstate Biotechnologies) tyrosine kinase activity are analyzed in an Elisa format. The Boehringer Mannheim Tyrosine Kinase Assay Kit (Catalog number 1-534505) with a cdc2 substrate peptide containing Tyr15 is used for the assay. HRP-conjugated anti-phosphotyrosine is used to detect phosphorylated peptide via a color reaction. Conditions recommended by the manufacturer are employed.

Reaction conditions: Five microliter aliquots of each compound prepared fresh at the time of the assay are added as a solution in 10 mM HEPES pH 7.5, 10% DMSO to the reaction well. Thirty-five microliters of reaction mix containing Src, buffer and peptide/bovine serum albumin mix are added to the compound wells and incubated at 30° C. for 10 minutes (reaction buffer: 50 mM TrisHCl pH 7.5, 10 mM $MgCl_2$, 0.1 mM EGTA, 0.5 mM $Na_3VO_4$). The reaction is started by addition of 10 microliters of ATP, incubated at 30° C. for 1 hour, and stopped by addition of 20 microliters of 0.5M EDTA. The reaction mixture with the phosphorylated peptide is then transferred to a streptavidin-coated microtiter plate (provided in the kit) and allowed to bind for 20 minutes. Unbound peptide and reaction mixture is decanted and the plate is washed with PBS six times. Horseradish peroxidase-conjugated phosphotyrosine antibody supplied in the kit is incubated with the plate for one hour, then decanted. The plate is again ished with PBS six times. Substrate (provided in the kit) is added and absorbance at 405 nm is measured.

Activity is determined as % inhibition as calculated by the formula:

(1-Abs/Abs(max))×100=% inhibition.

Where multiple concentrations of the test agent are used, an $IC_{50}$ (concentration which gives 50% inhibition) could be determined.

The results obtained for representative compounds of this invention are listed in Table 1.

Raf/Mek Kinase Cascade Assay Procedure

Raf-1 (c-Raf) is used to phosphorylate and activate inactive GST-MEK1 which then can phosphorylate and activate inactive p42 GST-MAPK, which subsequently is measured for phosphorylation of the TEY sequence (aa's 202-204) by a phospho-specific antibody from Sigma (cat. # 77439219041) Reagents: Sf9 insect cell lysate containing full length 6his-tagged recombinant human c-Raf. (Specific Activity: ~200 U/ml). Human Non-active Mek-1-GST and human GST-MAP kinase (recombinant proteins produced in E. coli).

Stock Solutions Raf/Mek Cascade Assay:
1. Assay Dilution Buffer (ADB): 20 mM MOPS, pH 7.2, 25 mM β-glycerol phosphate, 5 mM EGTA, 1 mM sodium orthovanadate, 1 mM dithiothreitol;
2. Magnesium/ATP Cocktail: 500 μM cold ATP and 75 mM magnesium chloride in ADB;
3. Active Kinase: Human Active c-Raf: Use at 0.4 U per assay point;
4. Non-active GST-MEK1: Use at 0.1 μg per assay point; and
5. Non-active GST-p42 MAP Kinase: Use at 1.0 μg per assay point.

Stock Solutions ELISA:
1. TBST-Tris (50 mM, pH 7.5), NaCl (150 mM), Tween-20 (0.05%);
2. Superblock (Pierce);
3. Anti-GST Ab (Pharmacia);
4. Anti-Phospho MAPK (Sigma); and
5. Anti-Mouse Ab/Europium conjugate (Wallac).

Assay Procedure:

First Stage: c-Raf Dependent Activation of GST-MEK and GST-MAPK
1. Add 20 ml of ADB per assay (i.e. per well of a 96 well plate);
2. Add 10 ml of 0.5 mM cold ATP and 75 mM magnesium chloride in ADB;
3. Add 2 ml of c-Raf (0.4 U/assay), in conjunction with 1.6ml non-active MEK1 (0.4 mg/assay);
4. Add 4 ml of non-active GST-p42 MAP Kinase (1.0 mg/assay);
5. Incubate for 60 minutes at 30° C. in a shaking incubator;
6. Transfer this mixture to an anti-GST Ab coated 96 well plate (Nunc Immunosorb plates coated o/n with a-GST, then blocked with Pierce Superblock);
7. Incubate for 60 minutes at 30° C. in a shaking incubator;
8. Wash 3× with TBST, add Anti-Phospho MAPK (Sigma) (1:3000);
9. Incubate for 60 minutes at 30° C. in a shaking incubator;
10. Wash 3× with TBST, add Anti-Mouse Ab/Europium conjugate (Wallac) (1:500);
11. Incubate for 60 minutes at 30° C. in a shaking incubator;
12. Wash 3× with TBST, Read plates in Wallac Victor model Plate Reader; and
13. Collect data analyze in Excel for single point and IC50 determinations.

Single point assay– % inhibition at 10 mg/ml (% Inhibition=1–cpd.treated sample/untreated control). $IC_{50}$ determinations–done on compounds from single point assays with >80% inhibition. Typically, the Raf/Mek assay is run at compound concentrations from 10 μM to 1 nM in half log dilutions. (% inhibition is determined for each compound concentration). The results obtained measure Raf and/or Mek kinase inhibition, and for representative compounds of this invention are listed in Table 1.

TABLE 1

Inhibition of Raf and/or Mek kinase (Raf/Mek), Mitogen Activated Protein Kinase (Mek-Erk) and $p60^{c-src}$ (Src)

| Example | Raf/Mek IC50 (μM) | Mek-Erk IC50 (μM) | Src IC50 (μM) |
|---|---|---|---|
| 11 | 0.114 (b) | | 0.281 (a) |
| 12 | 0.210 (c) | | |
| 13 | 1.427 | | |
| 14 | 0.795 (a) | | |
| 15 | 1.721 | | |
| 16 | 0.035 | | |
| 17 | 0.320 | | |
| 18 | 0.075 | | |
| 19 | 0.199 | | |

TABLE 1-continued

Inhibition of Raf and/or Mek kinase (Raf/Mek), Mitogen Activated Protein Kinase (Mek-Erk) and p60$^{c\text{-}src}$ (Src)

| Example | Raf/Mek IC50 (µM) | Mek-Erk IC50 (µM) | Src IC50 (µM) |
|---|---|---|---|
| 20 | 0.293 | | |
| 21 | 0.181 | | |
| 22 | 0.273 | | |
| 23 | 0.188 | | |
| 28 | 2.390 | | |
| 29 | 1.644 (b) | | |
| 30 | 0.220 (a) | | |
| 32 | 0.020 | 0.045 | |
| 33 | 0.003 | | |
| 34 | 0.250 | | 0.00055 |
| 35 | | | 0.001 |

(a) Average of two runs
(b) Average of three runs
(c) Average of four runs

Cell Proliferation Test Procedure for Inhibitors of Src Kinase

HT-29 cells: Compound effectiveness at inhibiting cell proliferation on plastic is performed in a 96-well format by plating 5000 cells per well in appropriate medium on day one, followed by compound addition on day 2 in serial two-fold dilutions. On day five, compound is washed away and medium containing MTS reagent (Promega) is added. Relative cell number is determined by reading the absorbance at 490 nm of a dye produced by an NAD-dependent cellular enzymatic reaction. These data are shown below in Table 2.

Anchorage Independent Src-transformed Fibroblast Proliferation Test Procedure: Rat2 fibroblasts stably transformed with a plasmid containing a CMV promotor controlled v-Src/Hu c-Src fusion gene in which the catalytic domain of human c-Src is inserted in place of the v-Src catalytic domain in the v-Src gene are used for the measurement of src dependent suspension growth. Ultra-low cluster plates (Costar # 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition=(Abs490 nm sample−blank)/(Abs490 nm no cmpd control−blank)×100%. These data are shown below in Table 2.

TABLE 2

Inhibition of Cancer Cell Growth

| Example | HT-29 prolif $IC_{50}$ (µM) | Src TF prolif $IC_{50}$ (µM) |
|---|---|---|
| 31 | | 2.4 |
| 34 | 2.6 | 0.466 |
| 35 | 2.7 | 0.140 |

Cell Based Screen for Inhibitors of Raf and/or Mek Kinase.

Materials

Cell Lines: Human adenocarcinoma cell line LoVo, known to be growth inhibited by low nM concentrations of a reference standard inhibitor of Ras and human adenocarcinoma cell line CaCo-2, known to be growth resistant to the same reference compound.

Cell Media: RPMI 1640 with 10% Fetal Bovine Serum supplemented with L-glutamine and Pennicilin/Streptomycin.

Compounds: Supplied usually as a 10 mM stock in 100% DMSO.

Normal Saline: 150 mM NaCl

Trichloroacetic Acid (TCA): 50% (w/v) in water

Sulforhodamine B (SRB): 0.4% (w/v) in 1% Acetic Acid

Tris Base: 10 mM in water

Methods

Cells are plated at 2000 cells per well for cell line LoVo and 1500 cells for cell line CaCo-2 in 96 well plates. Cells are plated in media (200 µl) and allowed to adhere overnight at 37° C. At 24 hours post plating, compounds are added directly at a volume of 0.5 µl. For the qualitative screen (compounds screened at 25 µM) compound is added directly to cells. For the quantitative screen, compound is first diluted in DMSO to generate concentrations of compound or reference standard of: 1, 5, 10 and 25 µM. It is advisable to make the dilutions in an identical 96 well plate so that compounds can be added using a multichannel micropipettor set at 0.5 µl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 µl of normal saline is then added to each well using an 8 well multichannel pipettor, followed by the careful addition of 50 µl of 50% TCA. The plates are then incubated for 2 hours at 4° C., after which the supernatant is removed using the same technique as above and the plated cells are washed twice with 200 µl water. The plates are then air dried and 50 µl of SRB stock solution is carefully added so that the entire bottom of each well is covered. This again can be done using an 8 well multichannel pipettor. The SRB is incubated with fixed cells for 15 minutes at room temperature after which the SRB is removed with the manifold as described above and the plates washed twice with 350 µl of 1% acetic acid per well each time. The plates are then air dried after which the bound SRB is released from protein by the addition of 200 µl of Tris base. Resolubilizing the SRB is aided by placing the plates on a rotator for 15-30 minutes. The absorbance of each well is determined at 550 or 562 nm using a microtiter plate reader.

Each compound or dilution thereof is performed in triplicate. Outliers are identified by visual inspection of the data. Each plate should have a "0" control (vehicle only).

Qualitative screen: To calculate % inhibition of a compound at 25 µM, the following formula is used: 1−(experimental absorbance @ 25 µM compound/"0" control absorbance)×100=% inhibition at 25 µM. Compounds having >50% inhibition at 25 µM are placed in the quantitative assay.

Quantitative Assay: A standard curve is constructed by plotting the concentration of compound against the average absorbance calculated at that concentration. A curve is plotted and the concentration at which the curve passes through the 50% the absorbance mark seen in the "0" control well is the $IC_{50}$ calculated for that compound. Multiple entries for a given compound indicate that it is tested multiple times. The results obtained for representative compounds of this invention are listed in Table 3.

TABLE 3

| Example | LoVo IC50 μM | BxPC3 IC50 μM |
|---|---|---|
| 11 | 0.029 (c) | 0.042 (b) |
| 12 | 0.46 (b) | 1.4 |
| 13 | 0.47 | 0.6 |
| 14 | 0.37 | 0.3 |
| 15 | 0.261 | 0.36 |
| 16 | 0.009 | 0.03 (b) |
| 17 | 0.031 | |
| 18 | 0.027 | 0.03 |
| 19 | 0.008 | |
| 20 | 0.022 | 0.038 |
| 21 | 0.02 | |
| 22 | 0.08 | |
| 23 | 0.474 | |
| 28 | 0.014 | 0.008 (b) |
| 29 | 0.004 | 0.008 (a) |
| 30 | 0.014 | 0.03 |
| 32 | 0.9 | |
| 33 | 0.047 | 0.049 (a) |

(a) Average of two runs
(b) Average of three runs
(c) Average of five runs

The results shown in tables 1, 2, 3, 4 and 5 demonstrate that the compounds of this invention are potent inhibitors of protein kinases, and are useful as described above.

The preparation of representative examples of the compounds of this invention is described below.

EXAMPLE 1

4-[3-Chloro-4-(1-methyl-1H-imidazole-2-ylsulfanyl)-phenylamino]-7-fluoro-6-methoxyquinoline-3-carbonitrile A mixture of 1.0 g (4.23 mmol) of 4-chloro-7-fluoro-6-methoxyquinoline-3-carbonitrile (AM100856), 1.114 g (4.65 mmol) of 3-chloro-4-(1-methyl-1H-imidazole-2-ylsulfanyl)phenylamine and 0.489 g (4.23 mmol) of pyridine hydrochloride in 10 mL of 2-ethoxyethanol is heated at 120° C. for 1.5 hours, then cooled to room temperature. The resulting solid is filtered, washed with cold 2-ethoxyethanol, then ethyl acetate. After drying in vacuo, the solid is suspended in a saturated solution of sodium bicarbonate, stirred for 45 minutes and collected by filtration. The reaction product is washed with water and dried in vacuo, to provide 4-[3-chloro-4-(1-methyl-1H-imidazole-2-ylsulfanyl)-phenylamino]-7-fluoro-6-methoxyquinoline-3-carbonitrile as a tan solid, mp 295-297° C.
MS (ES, positive ion mode): m/z calcd for $C_{21}H_{15}ClFN_5OS$: 439.1. found: 439.8 $(M+H)^+$

EXAMPLE 2

7-Fluoro-6-methoxy-4-[4-(pyridin-2-ylsulfanyl)-phenylamino]quinoline-3-carbonitrile Following the procedure of Example 1, a mixture of 635.4 mg (2.68 mmol) 4-chloro-7-fluoro-6-methoxy-quinoline-3-carbonitrile, 542.1 mg (2.81 mmol) of 4-(pyridin-2-ylsulfanyl)phenylamine and 309.8 mg (2.68 mmol) of pyridine hydrochloride are refluxed in 2-ethoxyethanol (27 mL) at 100° C. for 12 hours to provide 830 mg of 7-fluoro-6-methoxy-4-[4-(pyridin-2-ylsulfanyl)-phenylamino]-quinoline-3-carbonitrile as an off-white solid, mp 231-233° C.
MS (ES, positive mode): m/z calcd for $C_{22}H_{15}FN_4OS$: 402.1. Found 403.2 (M+1)

EXAMPLE 3

4-[3-Chloro-4-(pyridin-2-ylsulfanyl)-phenylamino]-7-fluoro-6-methoxyquinoline-3-carbonitrile Following the procedure of Example 1, a mixture of 635.4 mg (2.68 mmol) 4-chloro-7-fluoro-6-methoxy-quinoline-3-carbonitrile, 642.1 mg (2.81 mmol) of 3-chloro-4-(pyridin-2-ylsulfanyl)-phenylamine and 309.8 mg (2.68 mmol) of pyridine hydrochloride are refluxed in 2-ethoxyethanol (27 mL) at 100° C. for 12 hours to yield 4-[3-chloro-4-(pyridin-2-ylsulfanyl)-phenylamino]-7-fluoro-6-methoxyquinoline-3-carbonitrile as a yellow solid, mp 225-228° C.
MS (ES, positive mode): m/z calcd for $C_{22}H_{14}ClFN_4OS$: 436.1. Found 437.0 (M+1)

EXAMPLE 4

7-Fluoro-6-methoxy-4-[4-(pyridin-3-yloxy)-phenylamino]-quinoline-3-carbonitrile

Following the procedure of Example 1, a mixture of 635.4 mg (2.68 mmol) 4-chloro-7-fluoro-6-methoxy-quinoline-3-carbonitrile, 500 mg (2.81 mmol) of 4-(pyridin-3-yloxy)phenylamine and 309.8 mg (2.68 mmol) of pyridine hydrochloride are refluxed in 2-ethoxyethanol (27 mL) at 100° C. for 12 hours to yield 7-fluoro-6-methoxy-4-[4-(pyridin-3-yloxy)-phenylamino]-quinoline-3-carbonitrile as an off-white solid, mp 235-236° C.
MS (ES, positive mode): m/z calcd for $C_{22}H_{15}FN_4O_2$: 386.1. Found 387.2 (M+1)

EXAMPLE 5

7-Fluoro-6-methoxy-4-[4-(2-methoxy-phenoxy)phenylamino]quinoline-3-carbonitrile

Following the procedure of Example 1, a mixture of 626 mg (2.65 mmol) 4-chloro-7-fluoro-6-methoxy-quinoline-3-carbonitrile, 600 mg (2.79 mmol) of 7-fluoro-6-methoxy-4-[4-(2-methoxyphenoxy)phenylamino]quinoline-3-carbonitrile and 310 mg (2.65 mmol) of pyridine hydrochloride are refluxed in 2-ethoxyethanol (7 mL) at 120° C. for 30 minutes to yield 7-fluoro-6-methoxy-4-[4-(2-methoxy-phenoxy)phenylamino]quinoline-3-carbonitrile as a white solid, mp 146-150° C.
MS (ES, positive mode): m/z calcd for $C_{24}H_{18}FN_3O_3$: 415.4. Found 416.2 (M+1)

EXAMPLE 6

4-({3-Chloro-4-[(1-methyl-1H-imidazole-2-yl)thio]phenyl}amino)-7-fluoroquinoline-3-carbonitrile Following the procedure of Example 1, a mixture of 1.2 g (5.81 mmol) 4-chloro-7-fluoro-3-quinolinecarbonitrile, 1.53 g (6.39 mmol) of 3-chloro-4-(1-methyl-1H-imidazole-2-yl-sulfanyl)phenylamine and 0.671 g (5.81 mmol) of pyridine hydrochloride are refluxed in 2-ethoxyethanol (12 mL) at 120° C. for 45 minutes to yield 4-({3-chloro-4-[(1-methyl-1H-imidazole-2-yl)thio]phenyl}amino)-7-fluoroquinoline-3-carbonitrile as an off-white solid, mp 268-272° C.
MS (ES, negative mode): m/z calcd for $C_{20}H_{13}ClFN_5S$: 409.9. Found 408.1, 410.1 (M−1)

EXAMPLE 7

4-({3-Chloro-4-[(1-methyl-1H-imidazole-2-yl)sulfanyl]phenyl}amino)-6-ethoxy-7-fluoro-3-quinolinecarbonitrile Following the procedure of Example 1, a mixture of 2.4 g (9.72 mmol) 4-chloro-6-ethoxy-7-fluoro-3-quinolinecarbonitrile, 2.56 g (10.7 mmol) of 3-chloro-4-(1-methyl-1H-imidazole-2-ylsulfanyl)phenylamine and 1.2 g (10.38 mmol) of pyridine hydrochloride are refluxed in 2-ethoxyethanol (30 mL) at 110°0 C. for 1 hour to yield 4-({3-chloro-4-[(1-methyl-1H-imidazole-2-yl)sulfanyl]phenyl}amino)-6-ethoxy-7-fluoro-3-quinolinecarbonitrile as a pink solid, mp 251-254° C.

MS (ES, positive mode): m/z calcd for $C_{22}H_{17}ClFN_5OS$: 453.9. Found 454.3, 456.3 (M+1)

EXAMPLE 8

7-(2-Chloroethoxy)-6-methoxy-4-(4-phenoxyphenylamino)quinoline-3-carbonitrile

Following the procedure of Example 1, a mixture of 3.0 g (0.01 mol) of 4-chloro-7-(2-chloroethoxy)-6-methoxy-3-quinolinecarbonitrile (Boschelli, Diane H.; Ye, Fei; Wang, Yanong D.; Dutia, Minu; Johnson, Steve L.; Wu, Biqi; Miller, Karen; Powell, Dennis W.; Yaczko, Deanna; Young, Mairead; Tischler, Mark; Arndt, Kim; Discafani, Carolyn; Etienne, Carlo; Gibbons, Jay; Grod, Janet; Lucas, Judy; Weber, Jennifer M.; Boschelli, Frank. J. Med. Chem. 2001, 44, 3965-3977), 2.04 g (0.011 mol) of 4-phenoxyaniline and pyridine hydrochloride 1.16 g (0.01 mol) in 100 mL of 2-ethoxyethanol is heated at 135° C. for 2 hours. Water is added to the reaction mixture, and the precipitate is filtered off. After washing with water, ether and ethyl acetate, the solid is dried in vacuo to provide 3.48 g of 7-(2-chloroethoxy)-6-methoxy-4-(4-phenoxyphenylamino)quinoline-3-carbonitrile as a yellow solid, mp 148-151° C.

MS (ES, positive ion mode): m/z calcd for $C_{26}H_{20}ClN_3O_3$: 445.12. Found: 446.0; 448.0 (M+1)

EXAMPLE 9

4-{3-Chloro-4-[(1-methyl-1H-imidazole-2-yl)sulfanyl]anilino}-7-(3-chloropropoxy)-6-methoxy-3-quinolinecarbonitrile A 2.0 g (6.43 mmol) portion of 4-chloro-7-(3-chloropropoxy)-6-methoxy-3-quinolinecarbonitrile (Boschelli, Diane H.; Ye, Fei; Wang, Yanong D.; Dutia, Minu; Johnson, Steve L.; Wu, Biqi; Miller, Karen; Powell, Dennis W.; Yaczko, Deanna; Young, Mairead; Tischler, Mark; Arndt, Kim; Discafani, Carolyn; Etienne, Carlo; Gibbons, Jay; Grod, Janet; Lucas, Judy; Weber, Jennifer M.; Boschelli, Frank. J. Med. Chem. 2001, 44, 3965-3977) in 2-ethoxyethanol (20 mL) is heated to 60° C. To this is added 1.7 g (7.10 mmol) of 3-chloro-4-(1-methyl-1H-imidazole-2-ylsulfanyl)phenylamine (U.S. Pat. No. 4,973,599) and 0.74 g (6.43 mmol) of pyridine hydrochloride, and the resulting mixture is refluxed for 2 hours. After cooling, the precipitated solid is filtered, washed with aqueous sodium bicarbonate and dried in vacuo to give 2.93 g of 4-{3-chloro-4-[(1-methyl-1H-imidazole-2-yl)sulfanyl]anilino}-7-(3-chloropropoxy)-6-methoxy-3-quinolinecarbonitrile as a tan solid, mp 271-276° C.

MS (ES, positive ion mode): m/z calcd for $C_{24}H_{21}Cl_2N_5O_2S$: 514.5. Found: 514.1; 516.1 (M+1)

EXAMPLE 10

7-(2-Chloroethoxy)-4-(3-chloro-4-[(1-methyl-1H-imidazole-2-yl)sulfanyl]anilino}-6-methoxy-3-quinolinecarbonitrile Following the procedure of Example 9, 1.0 g (3.36 mmol) of 4-chloro-7-(2-chloroethoxy)-6-methoxy-3-quinolinecarbonitrile (Boschelli, Diane H.; Ye, Fei; Wang, Yanong D.; Dutia, Minu; Johnson, Steve L.; Wu, Biqi; Miller, Karen; Powell, Dennis W.; Yaczko, Deanna; Young, Mairead; Tischler, Mark; Arndt, Kim; Discafani, Carolyn; Etienne, Carlo; Gibbons, Jay; Grod, Janet; Lucas, Judy; Weber, Jennifer M.; Boschelli, Frank. J. Med. Chem. 2001, 44, 3965-3977) is reacted with 0.9 g (3.7 mmol) of 3-chloro-4-(1-methyl-1H-imidazole-2-ylsulfanyl)phenylamine (U.S. Pat. No. 4,973,599) and 0.4 g (3.46 mmol) of pyridine hydrochloride in 2-ethoxyethanol (10 mL) to provide 1.44 g of 7-(2-chloroethoxy)-4-{3-chloro-4-[(1-methyl-1H-imidazole-2-yl)sulfanyl]anilino}-6-methoxy-3-quinolinecarbonitrile as a tan solid, mp 278-280° C.

MS (ES, positive ion mode): m/z calcd for $C_{23}H_{19}Cl_2N_5O_2S$: 500.4. Found: 499.8; 501.7 (M+1)

EXAMPLE 11

4-({3-chloro-4-[(1-methyl-1H-imidazole-2-yl)thio]phenyl}amino)-6-methoxy-7-(4-pyrrolidin-1-ylpiperidin-1-yl)quinoline-3-carbonitrile A mixture of 150 mg (0.34 mmol) of 4-[3-chloro-4-(1-methyl-1H-imidazole-2-ylsulfanyl)-phenylamino]-7-fluoro-6-methoxyquinoline-3-carbonitrile and 316 mg (2.05 mmol) of 4-pyrrolidin-1-yl-piperidine in 1 mL of 1-methyl-2-pyrrolidinone is heated at 105° C. for 16 hours. The solvents are removed in vacuo. A 10 mL portion of water is added to the residue, from which a tan solid is precipitated out. The solid is filtered off and washed with water. After drying in vacuo, the solid is suspended in ethyl acetate and stirred for 1 hour. The solid is filtered off, washed with ethyl acetate and dried in vacuo to provide 140 mg of 4-[3-chloro-4-(1-methyl-1H-imidazole-2-ylsulfanyl)-phenylamino]-6-methoxy-7-(4-pyrrolidin-1-yl-piperidin-1-yl)-quinoline-3-carbonitrile as a yellow solid, mp 225-229° C.

MS (ES, positive ion mode): m/z calcd for $C_{30}H_{32}ClN_7OS$: 573.2. Found: 574.1; 576.1 (M+1)

EXAMPLE 12

6-Methoxy-4-{[4-(2-methoxyphenoxy)phenyl]amino}-7-(4-pyrrolidin-1-ylpiperidin-1-yl)quinoline-3-carbonitrile, trifluoroacetate salt Following the procedure of Example 11, a mixture of 50 mg (0.12 mmol) of 7-fluoro-6-methoxy-4-[4-(2-methoxyphenoxy)phenylamino]quinoline-3-carbonitrile and 111 mg (0.72 mmol) of 4-(1-pyrrolidinylpiperidine) in 0.5 mL of 1-methyl 2-pyrrolidinone is heated at 105° C. for 28 hours to yield the crude product. Purification by a Gilson HPLC (gradient solvents) gives 20 mg of 6-methoxy-4-{[4-(2-methoxyphenoxy)phenyl]amino}-7-(4-pyrrolidin-1-ylpiperidin-1-yl)quinoline-3-carbonitrile, trifluoroacetate salt as a brown oil.

MS (ES, positive ion mode): m/z calcd for $C_{33}H_{35}N_5O_3$: 549.7. Found: 550.5 (M+1)

EXAMPLE 13

6-Methoxy-4-[4-(pyridin-2-ylsulfanyl)-phenylamino]-7-(4-pyrrolidin-1-yl-piperidin-1-yl)-quinoline-3-carbonitrile Following the procedure of Example 11, a mixture of 150 mg (0.37 mmol) of 7-fluoro-6-methoxy-4-[4-(pyridin-2-ylsulfanyl)-phenylamino]-quinoline-3-carbonitrile, 287 mg (1.86 mmol) of 4-(1-pyrrolidinylpiperidine) are refluxed in 1-methyl 2-pyrrolidinone (1 mL) at 105° C. for 12 hours to yield the crude product. Purification by silica gel chromatography (95:5 methylene chloride/methanol) gives 107 mg of 6-methoxy-4-[4-(pyridin-2-ylsulfanyl)-phenylamino]-7-(4-pyrrolidin-1-yl-piperidin-1-yl)quinoline-3-carbonitrile as a yellow solid, mp 182-184° C.

MS (ES, positive mode): m/z calcd for $C_{31}H_{32}N_6OS$: 536.2. Found 537.3 (M+1)

EXAMPLE 14

4-[3-Chloro-4-(pyridin-2-ylsulfanyl)-phenylamino]-6-methoxy-7-(4-pyrrolidin-1-yl-piperidin-1-yl)-quinoline-3-carbonitrile Following the procedure of Example 11, a mixture of 150 mg (0.34 mmol) of 4-[3-Chloro-4-(pyridin-2-ylsulfanyl)-phenylamino]-7-fluoro-6-methoxyquinoline-3-carbonitrile and 264 mg (1.71 mmol) of 4-(1-pyrrolidinylpiperidine) are refluxed in 1-methyl 2-pyrrolidinone (1 mL) at 105° C. for 12 hours to yield the crude product. Purification by silica gel chromatography (95:5 methylene chloride/methanol) gives 126 mg of 4-[3-chloro-4-(pyridin-2-ylsulfanyl)-phenylamino]-6-methoxy-7-(4-pyrrolidin-1-yl-piperidin-1-yl)quinoline-3-carbonitrile as a yellow solid, mp 203-205° C.

MS (ES, positive mode): m/z calcd for $C_{31}H_{31}ClN_6OS$: 570.2. Found 571.3 (M+1)

EXAMPLE 15

6-Methoxy-4-[4-(pyridin-3-yloxy)-phenylamino]-7-(4-pyrrolidin-1-yl-piperidin-1-yl)-quinoline-3-carbonitrile Following the procedure of Example 11, a mixture of 150 mg (0.39 mmol) of 7-fluoro-6-methoxy-4-[4-(pyridin-3-yloxy)-phenylamino]-quinoline-3-carbonitrile and 299 mg (1.94 mmol) of 4-(1-pyrrolidinylpiperidine) are refluxed in 1-methyl 2-pyrrolidinone (1 mL) at 105° C. for 12 hours to yield the crude product. Purification by silica gel chromatography (95:5 methylene chloride/methanol) gives 120 mg of 6-methoxy-4-[4-(pyridin-3-yloxy) phenylamino]-7-(4-pyrrolidin-1-yl-piperidin-1-yl)quinoline-3-carbonitrile as a yellow solid, mp 194-196° C.

MS (ES, positive mode): m/z calcd for $C_{31}H_{32}N_6O_2$: 520.6. Found 521.3 (M+1)

EXAMPLE 16

4-({3-Chloro-4-[(1-methyl-1H-imidazole-2-yl)thio]phenyl}amino)-7-(4-pyrrolidin-1-ylpiperidin-1-yl)quinoline-3-carbonitrile Following the procedure of Example 11, a mixture of 150 mg (0.37 mmol) of 4-({3-chloro-4-[(1-methyl-1H-imidazole-2-yl)thio]phenyl}amino)-7-fluoroquinoline-3-carbonitrile and 339 mg (2.20 mmol) of 4-(1-pyrrolidinylpiperidine) in 1 mL of 1-methyl 2-pyrrolidinone is heated at 105° C. for 17 hours to yield the crude product. Purification by silica gel chromatography (gradient 98:2 methylene chloride/methanol to 9:1 methylene chloride/methanol) gives 66 mg of 4-({3-chloro-4-[(1-methyl-1H-imidazole-2-yl)thio]phenyl}amino)-7-(4-pyrrolidin-1-ylpiperidin-1-yl)quinoline-3-carbonitrile as a yellow solid, mp 125-130° C.

MS (ES, negative ion mode): m/z calcd for $C_{29}H_{30}ClN_7S$: 544.1. Found: 542.1; 543.9 (M–1)

EXAMPLE 17

4-({3-Chloro-4-[(1-methyl-1H-imidazole-2-yl)thio]phenyl}amino)-6-(2-methoxyethoxy)-7-(4-pyrrolidin-1-ylpiperidin-1-yl)quinoline-3-carbonitrile Following the procedure of Example 11, a mixture of 150 mg (0.31 mmol) of 4-({3-chloro-4-[(1-methyl-1H-imidazole-2-yl)sulfanyl]phenyl}amino)-7-fluoro-6-(2-methoxyethoxy)-3-quinolinecarbonitrile and 287 mg (1.86 mmol) of 4-(1-pyrrolidinylpiperidine) in 1 mL of 1-methyl 2-pyrrolidinone is heated at 105° C. for 17 hours to yield the crude product. Purification by silica gel chromatography (gradient 98:2 methylene chloride/methanol to 4:1 methylene chloride/methanol) gives 120 mg of 4-({3-chloro-4-[(1-methyl-1H-imidazole-2-yl)thio]phenyl}amino)-6-(2-methoxyethoxy)-7-(4-pyrrolidin-1-ylpiperidin-1-yl)quinoline-3-carbonitrile as a yellow solid, mp 238-241° C.

MS (ES, positive ion mode): m/z calcd for $C_{32}H_{36}ClN_7O_2S$: 635.2. Found: 635.4; 637.3 (M+1)

EXAMPLE 18

4-({3-chloro-4-[(1-methyl-1H-imidazole-2-yl)thio]phenyl}amino)-6-ethoxy-7-(4-pyrrolidin-1-ylpiperidin-1-yl)quinoline-3-carbonitrile Following the procedure of Example 11, a mixture of 150 mg (0.33 mmol) of 4-({3-chloro-4-[(1-methyl-1H-imidazole-2-yl)sulfanyl]phenyl}amino)-6-ethoxy-7-fluoro-3-quinolinecarbonitrile and 306 mg (1.98 mmol) of 4-(1-pyrrolidinylpiperidine) in 1 mL of 1-methyl 2-pyrrolidinone is heated at 105° C. for 17 hours to yield the crude product. Purification by silica gel chromatography (gradient 98:2 methylene chloride/methanol to 4:1 methylene chloride/methanol) gives 122 mg of 4-({3-chloro-4-[(1-methyl-1H-imidazole-2-yl)thio]phenyl}amino)-6-ethoxy-7-(4-pyrrolidin-1-ylpiperidin-1-yl)quinoline-3-carbonitrile as a yellow solid, mp 203-207° C.

MS (ES, positive ion mode): m/z calcd for $C_{31}H34ClN_7OS$: 588.2. Found: 588.3; 590.4 (M+1)

EXAMPLE 19

7-(1,4'-Bipiperidin-1'-yl)-4-({3-chloro-4-[(1-methyl-1H-imidazole-2-yl)thio]phenyl}amino)-6-methoxyquinoline-3-carbonitrile Following the procedure of Example 11, a mixture of 220 mg (0.5 mmol) of 4-[3-chloro-4-(1-methyl-1H-imidazole-2-ylsulfanyl)-phenylamino]-7-fluoro-6-methoxyquinoline-3-carbonitrile and 290mg (1.72 mmol) of 4-piperidinopiperidine in 1.5 mL of 1-methyl 2-pyrrolidinone is heated at 105° C. for 17 hours to yield the crude product. Purification by silica gel chromatography (gradient 94:6 methylene chloride/methanol to 89:10:1 methylene chloride/methanol/ammonium hydroxide) gives 193 mg of 7-(1,4'-bipiperidin-1'-yl)-

4-({3-chloro-4-[(1-methyl-1H-imidazole-2-yl)thio] phenyl}amino)-6-methoxyquinoline-3-carbonitrile as a beige solid, mp 221-223° C.

MS (ES, positive ion mode): m/z calcd for $C_{31}H_{34}ClN_7OS$: 588.2. Found: 588.6 (M+1)

EXAMPLE 20

4-({3-Chloro-4-[(1-methyl-1H-imidazole-2-yl)thio] phenyl}amino)-6-methoxy-7-[4-(4-methylpiperazin-1-yl) piperidin-1-yl]quinoline-3-carbonitrile Following the procedure of Example 11, a mixture of 110 mg (0.25 mmol) of 4-[3-chloro-4-(1-methyl-1H-imidazole-2-ylsulfanyl)-phenylamino]-7-fluoro-6-methoxyquinoline-3-carbonitrile and 140 mg (0.76 mmol) of 1-methyl-4-piperidin-4-ylpiperazine in 0.8 mL of 1-methyl 2-pyrrolidinone is heated at 105° C. for 28 hours to yield the crude product. Purification by silica gel chromatography (gradient 94:6 methylene chloride/methanol to 84:15:1 methylene chloride/methanol/ammonium hydroxide) gives 100 mg of the 4-({3-chloro-4-[(1-methyl-1H-imidazole-2-yl)thio] phenyl}amino)-6-methoxy-7-[4-(4-methylpiperazin-1-yl) piperidin-1-yl]quinoline-3-carbonitrile as a beige solid, mp 235-237° C.

MS (ES, positive ion mode): m/z calcd for $C_{31}H_{35}ClN_8OS$: 603.2. Found: 603.2 (M+1)

EXAMPLE 21

4-({3-Chloro-4-[(1-methyl-1H-imidazole-2-yl)thio] phenyl}amino)-6-methoxy-7-(4-morpholin-4-ylpiperidin-1-yl)quinoline-3-carbonitrile Following the procedure of Example 11, a mixture of 150 mg (0.33 mmol) of 4-[3-chloro-4-(1-methyl-1H-imidazole-2-ylsulfanyl)-phenylamino]-7-fluoro-6-methoxyquinoline-3-carbonitrile and 170 mg (1.0 mmol) of 1-methyl-4-piperidin-4-ylmorpholine in 1.0 mL of 1-methyl 2-pyrrolidinone is heated at 105° C. for 24 hours to yield the crude product. Purification by silica gel chromatography (gradient 97:3 methylene chloride/methanol to 9:1 methylene chloride/methanol) gave 100 mg of 4-({3-chloro-4-[(1-methyl-1H-imidazole-2-yl)thio]phenyl}amino)-6-methoxy-7-(4-morpholin-4-ylpiperidin-1-yl)quinoline-3-carbonitrile as a beige solid, mp 219-221° C.

MS (ES, positive ion mode): m/z calcd for $C_{30}H_{32}ClN_7O_2S$: 590.2. Found: 590.2; 592.1 (M+1)

EXAMPLE 22

4-({3-Chloro-4-[(1-methyl-1H-imidazole-2-yl)thio] phenyl}amino)-6-methoxy-7-[4-(1-methylpiperidin-4-yl)piperazin-1-yl]quinoline-3-carbonitrile Following the procedure of Example 11, a mixture of 220 mg (0.5 mmol) of 4-[3-chloro-4-(1-methyl-1H-imidazole-2-ylsulfanyl)-phenylamino]-7-fluoro-6-methoxyquinoline-3-carbonitrile, 290 mg (1.6 mmol) of 1-(1-methylpiperidin-4-yl)piperazine in 1.2 mL of 1-methyl 2-pyrrolidinone is heated at 105° C. for 20 hours to yield the crude product. Purification by silica gel chromatography (gradient 9:1 methylene chloride/methanol to 85:15 methylene chloride/methanol) gives 210 mg of 4-({3-chloro-4-[(1-methyl-1H-imidazole-2-yl)thio]phenyl}amino)-6-methoxy-7-[4-(1-methylpiperidin-4-yl)piperazin-1-yl]quinoline-3-carbonitrile as a beige solid, mp 220-226° C. (shrinks at 205° C.).

MS (ES, positive ion mode): m/z calcd for $C_{31}H_{35}ClN_8OS$: 603.2. Found: 603.2 (M+1)

EXAMPLE 23

4-({3-Chloro-4-[(1-methyl-1H-imidazole-2-yl)thio] phenyl}amino)-7-{4-[2-(1H-imidazole-1-yl)ethyl] piperazin-1-yl}-6-methoxyquinoline-3-carbonitrile Following the procedure of Example 11, a mixture of 220 mg (0.5 mmol) of 4-[3-chloro-4-(1-methyl-1H-imidazole-2-ylsulfanyl)-phenylamino]-7-fluoro-6-methoxyquinoline-3-carbonitrile and 290 mg (1.6 mmol) of 1-(2-imidazole-1-yl-ethyl)piperazine in 1.2 mL of 1-methyl 2-pyrrolidinone is heated at 105° C. for 20 hours to yield the crude product. Purification by silica gel chromatography (gradient 95:5methylene chloride/methanol to 85:15 methylene chloride/methanol) gives 210 mg of 4-({3-chloro-4-[(1-methyl-1H-imidazole-2-yl)thio]phenyl}amino)-7-{4-[2-(1H-imidazole-1-yl)ethyl]piperazin-1-yl}-6-methoxyquinoline-3-carbonitrile as a beige solid, mp 251-253° C.

MS (ES, positive ion mode): m/z calcd for $C_{30}H_{30}ClN_9OS$: 600.1. Found: 600.2 (M+1)

EXAMPLE 24

6-Nitro-4-oxo-7-(4-pyrrolidin-1-ylpiperidin-1-yl)-1,4-dihydroquinoline-3-carbonitrile A mixture of 1.3 g (5.21 mmol) of 7-chloro-4-hydroxy-6-nitro-3-quinolinecarbonitrile (U.S. Pat. No. 6,297,258) and 2.6 g (16.67 mmol) of 4-(1-pyrrolidine)piperidine 17.0 ml of 1-methyl 2-pyrrolidinone is heated at 120° C. for 5 hours. The mixture is cooled to room temperature and stirred with 15 mL of saturated solution of sodium bicarbonate. Following removal of solvents in vacuo, a residue is obtained, which is stirred with ether. The solid is collected by filtration and washed with ether. The crude product is dissolved in 9:1 methylene chloride/methanol, filtered through a pad of Celite (to remove inorganic material) and further washed with 9:1 methylene chloride/methanol. Evaporation of the filtrate to dryness yields a glassy residue. Purification by silica gel chromatography (gradient 9:1 methylene chloride/methanol to 4:1 methylene chloride/methanol) gives 1.3 g of 6-nitro-4-oxo-7-(4-pyrrolidin-1-ylpiperidin-1-yl)-1,4-dihydroquinoline-3-carbonitrile as an orange solid, mp 232-235° C.

MS (ES, positive ion mode): m/z calcd for $C_{19}H_{21}N_5O_3$: 367.4. Found: 368.2 (M+1)

EXAMPLE 25

4-chloro-6-nitro-7-(4-pyrrolidin-1-ylpiperidin-1-yl) quinoline-3-carbonitrile

A mixture of 1.3 g (3.54 mmol) of 6-nitr2o-4-oxo-7-(4-pyrrolidin-1-ylpiperidin-1-yl)-1,4-dihydroquinoline-3-carbonitrile, 20 ml of oxalyl chloride and 10 drops of dimethyl formamide in 20 ml of methylene chloride is heated under reflux for 2 hours. After allowing the mixture to cool to room temperature, the solvent is evaporated to dryness in vacuo. Toluene is added to the resulting residue and evaporated in vacuo. Following a second toluene addition/evaporation cycle, the resulting solid is cooled in an ice bath and neutralized with saturated solution of sodium bicarbonate. The resulting solid is collected by filtration and dried in vacuo to give 1.25 g of 4-chloro-6-nitro-7-(4-pyrrolidin-1-ylpiperidin-1-yl)quinoline-3-carbonitrile as a yellow solid, mp 255-265 (dec).

MS (ES, positive ion mode): m/z calcd for C19H20ClN5O2: 385.9. Found: 386.2 (M+1)

EXAMPLE 26

4-({3-Chloro-4-[(1-methyl-1H-imidazole-2-yl)thio] phenyl}amino)-6-nitro-7-(4-pyrrolidin-1-ylpiperidin-1-yl)quinoline-3-carbonitrile A mixture of 0.5 g (1.45 mmol) of 4-chloro-6-nitro-7-(4-pyrrolidin-1-ylpiperidin-1-yl)quinoline-3-carbonitrile, 0.38 g (1.6 mmol) of 3-chloro-4-[(1-methyl-1H-imidazole-2-yl) sulfanyl]aniline and 0.17 g of pyridine hydrochloride in 7.0 mL of 2-ethoxyethanol is heated at 105° C. for 1 hour. After cooling to room temperature, the mixture is stirred with 15 mL of saturated solution of sodium bicarbonate. The resulting solid is collected by filtration and washed with water. Some of the product dissolves in water, which is recovered by extracting the aqueous layer with solution of 95:5 methylene chloride/methanol. The organic layer is evaporated to provide crude product. The combined solids are purified by silica gel chromatography (gradient 95:5methylene chloride/methanol to 4:1 methylene chloride/methanol) gives 0.52 g of 4-({3-chloro-4-[(1-methyl-1H-imidazole-2-yl)thio] phenyl}amino)-6-nitro-7-(4-pyrrolidin-1-ylpiperidin-1-yl) quinoline-3-carbonitrile as an orange solid, mp 220-230° C.
MS (ES, positive ion mode): m/z calcd for $C_{29}H_{29}ClN_8O_2S$: 589.1. Found: 589.2 (M+H)

EXAMPLE 27

6-Amino-4-[3-chloro-4-(1-methyl-1H-imidazole-2-ylsulfanyl)phenylamino]-7-(4-pyrrolidin-1-yl-piperidin-1-yl)quinoline-3-carbonitrile To a refluxing mixture of 0.5 g (8.95 mmol) of iron powder, 0.7 g (13.1 mmol) of ammonium chloride and 14 mL of water is added 1.26 g (2.14 mmol) of 4-({3-chloro-4-[(1-methyl-1H-imidazole-2-yl)thio]phenyl}amino)-6-nitro-7-(4-pyrrolidin-1-yl-piperidin-1-yl)quinoline-3-carbonitrile in portions so as to maintain gentle reflux. The resulting mixture is heated under reflux for 45 minutes. The mixture is filtered hot through a pad of Celite, washed with ethanol, and the filtrate is evaporated to dryness to yield a residue. A saturated solution of sodium bicarbonate is added to the residue, and the mixture is stirred. The solid is collected by filtration, washed with water and dried to yield 1.2 g of 6-amino-4-[3-chloro-4-(1-methyl-1H-imidazole-2-ylsulfanyl)phenylamino]-7-(4-pyrrolidin-1-yl-piperidin-1-yl)quinoline-3-carbonitrile as a yellow solid, mp 265-267° C.
MS (ES, positive ion mode): m/z calcd for $C_{29}H_{31}ClN_8S$: 559.1. Found: 559.2 (M+1)

EXAMPLE 28

N-Acetyl-N-[4-[3-chloro-4-(1-methyl-1H-imidazole-2-ylsulfanyl)-phenylamino]-3-cyano-7-(4-pyrrolidin-1-yl-piperidin-1-yl)quinolin-6-yl]acetamide To a cold (0° C.-5° C.) solution of 1.2 g (2.14 mmol) of 6-amino-4-[3-chloro-4-(1-methyl-1H-imidazole-2-ylsulfanyl)phenylamino]-7-(4-pyrrolidin-1-yl-piperidin-1-yl) quinoline-3-carbonitrile and 3.6 ml (22.6 mmol) of N,N-diethyl aniline in 18 mL of 1-methyl 2-pyrrolidinone is added dropwise 1.6 ml (21.2 mmol) of acetyl chloride. The resulting mixture is stirred at room temperature for 4 hours. The solvent is removed in vacuo to yield a residue, which is triturated with ether. A saturated solution of sodium bicarbonate is added to the resulting solid and the mixture is stirred, collected by filtration and dried in vacuo. Purification by silica gel chromatography (gradient 95:5methylene chloride/methanol to 4:1 methylene chloride/methanol) gives 738 mg of N-acetyl-N-[4-[3-chloro-4-(1-methyl-1H-imidazole-2-ylsulfanyl)-phenylamino]-3-cyano-7-(4-pyrrolidin-1-yl-piperidin-1-yl) quinolin-6-yl]acetamide as a beige solid, mp 245-247° C.
MS (ES, positive ion mode): m/z calcd for $C_{33}H_{35}ClN_8O_2S$: 643.2. Found: 643.2 (M+1)

EXAMPLE 29

N-[4-({3-Chloro-4-[(1-methyl-1H-imidazole-2-yl) thio]phenyl}amino)-3-cyano-7-(4-pyrrolidin-1-ylpiperidin-1-yl)quinolin-6-yl]acetamide By the procedure of Example 27, 0.1 g (0.18 mmol) of 4-({3-chloro-4-[(1-methyl-1H-imidazole-2-yl)thio] phenyl}amino)-6-amino-7-(4-pyrrolidin-1-ylpiperidin-1-yl) quinoline-3-carbonitrile is reacted with 0.3 ml (1.9 mmol) of N,N-diethyl aniline and 0.04 ml (0.56 mmol) of acetyl chloride in 1.5 mL of NMP. The crude residue is purified by silica gel chromatography (gradient 95:5 methylene chloride/ methanol to 4:1 methylene chloride/methanol) to give 95 mg of N-[4-({3-chloro-4-[(1-methyl-1H-imidazole-2-yl)thio] phenyl}amino)-3-cyano-7-(4-pyrrolidin-1-ylpiperidin-1-yl) quinolin-6-yl]acetamide as a beige solid, mp 243-255° C.
MS (ES, positive ion mode): m/z calcd for $C_{31}H_{33}ClN_8OS$: 601.2. Found: 601.5 (M+1)

EXAMPLE 30

4-({3-Chloro-4-[(1-methyl-1H-imidazole-2-yl)thio] phenyl}amino)-6-(methylamino)-7-(4-pyrrolidin-1-ylpiperidin-1-yl)quinoline-3-carbonitrile A mixture of 130 mg (0.23 mmol) of 6-amino-4-[3-chloro-4-(1-methyl-1H-imidazole-2-ylsulfanyl)phenylamino]-7-(4-pyrrolidin-1-yl-piperidin-1-yl)quinoline-3-carbonitrile, 12.0 mg (0.4 mmol) of paraformaldehyde, 25.0 mg (0.39 mmol) of sodium cyanoborohydride and 2 drops of acetic acid in 15 mL of ethanol is heated under reflux for 8 hours. The mixture is cooled to room temperature and solvent removed in vacuo. A 12 mL solution of 1N sodium hydroxide is added to the residue, and the mixture is stirred. A crude solid is collected by filtration, washed with water and dried. Purification by silica gel chromatography (gradient 95:5 methylene chloride/ methanol to 4:1 methylene chloride/methanol) gives 66.0 mg of the 4-({3-Chloro-4-[(1-methyl-1H-imidazole-2-yl)thio] phenyl}amino)-6-(methylamino)-7-(4-pyrrolidin-1-ylpiperidin-1-yl)quinoline-3-carbonitrile as an yellow solid, mp 242-250° C.
MS (ES, positive ion mode): m/z calcd for $C_{30}H_{33}ClN_8S$: 573.2. Found: 573.3 (M+1)

EXAMPLE 31

4-[(2,4-dichloro-5-methoxyphenyl)amino]-6-methoxy-7-(4-pyrrolidin-1-ylpiperidin-1-yl)quinoline-3-carbonitrile Following the procedure of Example 11, a mixture of 200.0 mg (0.51 mmol) of 4-(2,4-dichloro-5-methoxyanilino)-7- fluoro-6-methoxy-3-quinolinecarbonitrile and 472.0 mg (3.06 mmol) of 4-(1-pyrrolidinyl)piperidine in 1.0 mL of 1-methyl-2-pyrrolidinone is heated in a sealed tube at 105° C. for 15 hours to yield the crude product. Purification by preparative thin layer chromatography (eluting with 4:1 dichloromethane/methanol) provides 116.5 mg of the pure product as a yellow solid, mp 225-227° C.

MS (ES, negative ion mode): m/z calcd for $C_{27}H_{29}Cl_2N_5O_2$: 525.2. Found: 524.3 (M-1)

EXAMPLE 32

7-(2-[1,4']Bipiperidinyl-1'-yl-ethoxy)-6-methoxy-4-(4-phenoxy-phenylamino)-quinoline-3-carbonitrile A mixture of 222.5 mg (0.5 mmol) of 7-(2-chloroethoxy)-6-methoxy-4-(4-phenoxyphenylamino)quinoline-3-carbonitrile, 841.4 mg (5.0 mmol) of 4-piperidinopiperidine and 49.5 mg (0.33 mmol) of sodium iodide in 6.0 mL of ethylene glycol dimethyl ether are heated in a sealed tube at 135-140° C. for 17 hours to yield the crude product. Solvents are removed in vacuo. Purification of the oily residue is carried out by preparative thin layer chromatography (eluting with 85:15 dichloromethane/methanol) to provide 137.7 mg of 7-(2-[1,4']bipiperidinyl-1'-yl-ethoxy)-6-methoxy-4-(4-phenoxy-phenylamino)-quinoline-3-carbonitrile as a light yellow solid, mp 141° C. (decompose).

MS (ES, positive ion mode): m/z calcd for $C_{35}H_{39}N_5O_3$: 577.3. Found: 578.1 (M+1)

EXAMPLE 33

4-{3-Chloro-4-[(1-methyl-1H-imidazole-2-yl)sulfanyl]anilino}-6-methoxy-7-{3-[4-(1-pyrrolidinyl)-1-piperidinyl]propoxy}-3-quinolinecarbonitrile A mixture of 150.0 mg (0.29 mmol) of 4-{3-chloro-4-[(1-methyl-1H-imidazole-2-yl)sulfanyl]anilino}-7-(3-chloropropoxy)-6-methoxy-3-quinolinecarbonitrile and 43.7 mg (0.29 mmol) of sodium iodide in 4.0 mL of piperidine are heated in a sealed tube at 115° C. for 5 hours to yield the crude product. After removal of the solvents in vacuo, water is added to the residue to precipitate out the crude product. The solid is filtered, then dissolved in dichloromethane/methanol. Purification is carried out by preparative thin layer chromatography (eluting with 9:1:0.1 dichloromethane/methanol/aqueous ammonium hydroxide) to provide 56.8 mg of 4-{3-chloro-4-[(1-methyl-1H-imidazole-2-yl)sulfanyl]anilino}-6-methoxy-7-{3-[4-(1-pyrrolidinyl)-1-piperidinyl]propoxy}-3-quinolinecarbonitrile as a beige solid, mp 196-198° C.

MS (ES, positive ion mode): m/z calcd for $C_{33}H_{38}ClN_7O_2S$: 631.3. Found: 631.8; 633.7 (M+1)

EXAMPLE 34

4-(2,4-Dichloro-5-methoxyanilino)-6-methoxy-7-{3-[4-(1-pyrrolidinyl)-1-7-{3-[4-(1-pyrrolidinyl)-1-piperidinyl]propoxy}-3-quinolinecarbonitrile A mixture of 250 mg (0.536 mmol) of 7-(3-chloropropoxy)-4-(2,4-dichloro-5-methoxyphenylamino)-6-methoxyquinoline-3-carbonitrile (Boschelli, Diane H.; Ye, Fei; Wang, Yanong D.; Dutia, Minu; Johnson, Steve L.; Wu, Biqi; Miller, Karen; Powell, Dennis W.; Yaczko, Deanna; Young, Mairead; Tischler, Mark; Arndt, Kim; Discafani, Carolyn; Etienne, Carlo; Gibbons, Jay; Grod, Janet; Lucas, Judy; Weber, Jennifer M.; Boschelli, Frank. J. Med. Chem. 2001, 44, 3965-3977) and 410 mg (2.68 mmol) of 4-pyrrolidin-1-yl-piperidine are heated in 2 mL of ethylene glycol dimethyl ether at 90° C. for 30 hours to yield the crude product. After adding water to the reaction mixture, the layers are separated. The organic layer is dried over sodium sulfate, which is removed by filtration. Following removal of the solvent in vacuo, the residue is recrystallized from ethyl acetate and ether to give 135 mg of 4-(2,4-dichloro-5-methoxyanilino)-6-methoxy-7-{3-[4-(1-pyrrolidinyl)-1-7-{3-[4-(1-pyrrolidinyl)-1-piperidinyl]propoxy}-3-quinolinecarbonitrile as an off-white solid, mp 108-112° C.

MS (ES, positive ion mode): m/z calcd for $C_{30}H_{35}Cl_2N_5O_3$: 584.5. Found: 584.4; 586.3 (M+1)

EXAMPLE 35

7-(3-[1,4'-Bipiperidin]-1'-ylpropoxy)-4-[(2,4-dichloro-5-methoxyphenyl)amino]-6-methoxy-3-quinolinecarbonitrile A mixture of 260 mg (0.56 mmol) of 7-(3-chloropropoxy)-4-(2,4-dichloro-5-methoxyphenylamino)-6-methoxyquinoline-3-carbonitrile (Boschelli, Diane H.; Ye, Fei; Wang, Yanong D.; Dutia, Minu; Johnson, Steve L.; Wu, Biqi; Miller, Karen; Powell, Dennis W.; Yaczko, Deanna; Young, Mairead; Tischler, Mark; Arndt, Kim; Discafani, Carolyn; Etienne, Carlo; Gibbons, Jay; Grod, Janet; Lucas, Judy; Weber, Jennifer M.; Boschelli, Frank. J. Med. Chem. 2001, 44, 3965-3977) and 380 mg (2.24 mmol) of [1,4']bipiperidinyl are heated in 3 mL of ethylene glycol dimethyl ether at 85° C. for sixteen hours to yield the crude product. Following removal of the solvent in vacuo, the crude product is purified by silica gel chromatography (eluting with 7:3 methylene chloride/methanol) to give 35 mg of 7-(3-[1,4'-bipiperidin]-1'-ylpropoxy)-4-[(2,4-dichloro-5-methoxyphenyl)amino]-6-methoxy-3-quinolinecarbonitrile as a white solid, mp 130-132° C.

MS (ES, positive ion mode): m/z calcd for $C_{31}H_{37}Cl_2N_5O_3$: 598.6. Found: 598.3; 600.3 (M+1)

EXAMPLE 36

4-{3-Chloro-4-[(1-methyl-1H-imidazole-2-yl)sulfanyl]anilino}-6-methoxy-7-{2-[4-(1-pyrrolidinyl)-1-piperidinyl]ethoxy}-3-quinolinecarbonitrile A mixture of 200 mg (0.40 mmol) of 7-(2-chloroethoxy)-4-{3-chloro-4-[(1-methyl-1H-imidazole-2-yl)sulfanyl]anilino}-6-methoxy-3-quinolinecarbonitrile and 1.5 g (10 mmol) of 4-pyrrolidin-1-yl-piperidine are heated in N,N-dimethylformamide at 85° C. for 5 hours and at 40° C. for 60 hours. The reaction mixture is poured slowly into saturated aqueous sodium bicarbonate to yield a solid which is subsequently filtered off. The crude solid is washed with water, then recrystallized from anhydrous ethyl ether to give 203 mg of 4-{3-chloro-4-[(1-methyl-1H-imidazole-2-yl)sulfanyl]anilino}-6-methoxy-7-{2-[4-(1-pyrrolidinyl)-1-piperidinyl]ethoxy}-3-quinolinecarbonitrile as an off-white solid, mp 127-130° C.

MS (ES, positive ion mode): m/z calcd for $C_{32}H_{36}ClN_7O_2S$: 618.2. Found: 617.8; 618.7 (M+1)

What is claimed is:

1. A compound of Formula 1

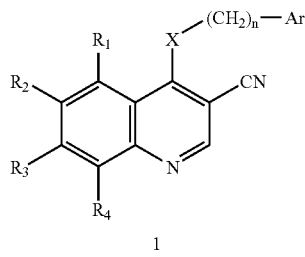

Formula 1 wherein:

Ar is a radical of the form:

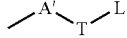

wherein;

A' is a phenyl ring; wherein the phenyl ring is optionally mono- or di-substituted with a substituent selected from an alkyl of 1-6 carbon atoms, an alkenyl of 2-6 carbon atoms, an alkynyl of 2-6 carbon atoms, azido, a hydroxyalkyl of 1-6 carbon atoms, a halogen, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, a N-alkylaminoalkyl of 2-9 carbon atoms, a N,N-dialkylaminoalkyl of 3-10 carbon atoms, an N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, a alkenoyloxy of 3-8 carbon atoms, an alkynoyloxy of 3-8 carbon atoms, a carbamoyl, a N-alkylcarbamoyl of 2-7 carbon atoms, a N,N-dialkylcarbamoyl of 3-13 carbon atoms, and benzoylamino;

T is substituted at a carbon of the phenyl ring with —O(CH$_2$)$_m$—, or —S(CH$_2$)$_m$—;

L is an imidazole, pyridyl or a phenyl ring wherein the imidazole, pyridyl or phenyl ring is optionally substituted at a carbon or nitrogen with one, two, or three substituents independently selected from an alkyl of 1-6 carbon atoms, an alkenyl of 2-6 carbon atoms, an alkynyl of 2-6 carbon atoms, azido, a hydroxyalkyl of 1-6 carbon atoms, a halogen, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, an N,N-dialkylaminoalkyl of 3-10 carbon atoms, a N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, a benzoylamino, a 5- or 6-membered heteroaryl ring where the heteroaryl ring contains 1 to 3 heteroatoms selected from N, O, and S and where the heteroaryl ring may be optionally mono- or di-substituted with a substituent independently selected from a halogen, an oxo, a thiocarbonyl, an alkyl of 1-6 carbon atoms, an alkenyl of 2-6 carbon atoms, an alkynyl of 2-6 carbon atoms, azido, a hydroxyalkyl of 1-6 carbon atoms, a halomethyl, an alkoxymethyl of 2-7 carbon atoms, an alkanoyloxymethyl of 2-7 carbon atoms, an alkoxy of 1-6 carbon atoms, an alkylthio of 1-6 carbon atoms, a hydroxy, a trifluoromethyl, a cyano, a nitro, a carboxy, an alkoxycarbonyl of 2-7 carbon atoms, an alkanoyl of 2-7 carbon atoms, a phenoxy, a phenyl, a thiophenoxy, a benzoyl, a benzyl, an amino, an alkylamino of 1-6 carbon atoms, a dialkylamino of 2 to 12 carbon atoms, a phenylamino, a benzylamino, an alkanoylamino of 1-6 carbon atoms, an alkenoylamino of 3-8 carbon atoms, an alkynoylamino of 3-8 carbon atoms, a carboxyalkyl of 2-7 carbon atoms, a carboalkoxyalkyl of 3-8 carbon atoms, an aminoalkyl of 1-5 carbon atoms, an N-alkylaminoalkyl of 2-9 carbon atoms, a N,N-dialkylaminoalkyl of 3-10 carbon atoms, a N-alkylaminoalkoxy of 3-9 carbon atoms, a N,N-dialkylaminoalkoxy of 4-10 carbon atoms, a mercapto, a methylmercapto, an alkanoyloxy of 1-6 carbon atoms, an alkenoyloxy of 3-8 carbon atoms, an alkynoyloxy of 3-8 carbon atoms, a carbamoyl, an N-alkylcarbamoyl of 2-7 carbon atoms, a N,N-dialkylcarbamoyl of 3-13 carbon atoms, and a benzoylamino;

m is 0;
n is 0;
X is NH;
R is alkyl of 1-6 carbon atoms;
$R_1$ and $R_4$ are a hydrogen;
$R_2$ is are a hydrogen, —OH or —OR where —OR is optionally substituted with —OH or —$C_1$-$C_6$alkoxy;
$R_3$ is piperidine or piperazine optionally linked to a second ring selected from piperidine, piperazine, pyrrolidine, morpholine, or imidazole, where said second ring is optionally substituted with $R_6$, and where said link is a bond or divalent straight or branched $C_1$-$C_4$alkyl;
$R_6$ is hydrogen, an alkyl of 1-6 carbon atoms, an alkenyl of 2-6 carbon atoms, an alkynyl of 2-6 carbon atoms, a cycloalkyl of 1-6 carbon atoms, an alkanoyl of 2-7 carbon atoms, a carbamoylalkyl of 2-7 carbon atoms, a hydroxyalkyl of 1-6 carbon atoms, a hydroxycycloalkyl of 3-6 carbon atoms, a carboxyalkyl of 2-7 carbon atoms, pyrrolidine, piperidine, or imidazole optionally substituted with methyl;
a crystalline form or a pharmaceutically acceptable salt thereof.

2. A compound of claim 1 wherein:
$R_1$ and $R_4$ are hydrogen;
$R_2$ is hydrogen, an alkoxy of one to four carbon atoms, a fluorine, or a nitro;
$R_3$ is piperidine or piperazine optionally substituted with pyrrolidine, piperidine, morpholine, imidazole optionally substituted with methyl;
X is NH;
n is 0;
Ar is a radical of the form:

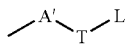

wherein;
A' is a pyridyl or phenyl optionally mono or di substituted with a halogen;
T is substituted at a carbon of the phenyl ring with —S($CH_2$)$_m$—, or —O($CH_2$)$_m$—;
m is 0;
L is imidazole. pyridyl or phenyl optionally substituted on a nitrogen with a methyl or a phenyl ring optionally substituted with one, two, or three substituents independently selected from an alkoxy of one carbon atom, a 5 or 6 membered heteroaryl ring wherein the heteroaryl ring contains 1 or 2 heteroatoms of N; or
a crystalline form or a pharmaceutically acceptable salt thereof.

3. A compound of claim 1 wherein:
$R_1$ and $R_4$ are hydrogen;
$R_2$ is an alkoxy of one carbon atom;
$R_3$ is piperidine substituted with pyrrolidine;
X is NH;
n is 0;
Ar is a radical of the form:

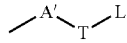

wherein;
A' is a phenyl ring optionally mono or di substituted with a chloride;
T is substituted at a carbon of the phenyl ring with —S($CH_2$)$_m$—,
m is 0;
L is imidazole, pyridyl or phenyl optionally substituted on a nitrogen with a methyl; or
a crystalline form or a pharmaceutically acceptable salt thereof.

4. A compound selected from 4-({3-chloro-4-[(1-methyl-1H-imidazole-2-yl)thio]phenyl}amino)-6-methoxy-7-(4-pyrrolidin-1-ylpiperidin-1-yl)quinoline-3-carbonitrile, 6-Methoxy-4-{[4-(2-methoxyphenoxy)phenyl]amino}-7-(4-pyrrolidin-1-ylpiperidin-1-yl)quinoline-3-carbonitrile, trifluoroacetate salt, 6-Methoxy-4-[4-(pyridin-2-ylsulfanyl)-phenylamino]-7-(4-pyrrolidin-1-yl-piperidin-1-yl)-quinoline-3-carbonitrile, 4-[3-Chloro-4-(pyridin-2-ylsulfanyl)-phenylamino]-6-methoxy-7-(4-pyrrolidin-1-yl-piperidin-1-yl)-quinoline-3-carbonitrile, 6-Methoxy-4-[4-(pyridin-3-yloxy)-phenylamino]-7-(4-pyrrolidin-1-yl-piperidin-1-yl)-quinoline-3-carbonitrile, 4-({3-Chloro-4-[(1-methyl-1H-imidazole-2-yl)thio]phenyl}amino)-7-(4-pyrrolidin-1-ylpiperidin-1-yl)quinoline-3-carbonitrile, 4-({3-Chloro-4-[(1-methyl-1H-imidazole-2-yl)thio]phenyl}amino)-6-(2-methoxyethoxy)-7-(4-pyrrolidin-1-ylpiperidin-1-yl) quinoline-3-carbonitrile, 4-({3-chloro-4-[(1-methyl-1H-imidazole-2-yl)thio]phenyl}amino)-6-ethoxy-7-(4-pyrrolidin-1-ylpiperidin-1-yl)quinoline-3-carbonitrile, 7-(1,4'-Bipiperidin-1'-yl)-4-({3-chloro-4-[(1-methyl-1H-imidazole-2-yl)thio]phenyl}amino)-6-methoxyquinoline-3-carbonitrile, 4-({3-Chloro-4-[(1-methyl-1H-imidazole-2-yl)thio]phenyl}amino)-6-methoxy-7-[4-(4-methylpiperazin-1-yl)piperidin-1-yl]quinoline-3-carbonitrile, 4-({3-Chloro-4-[(1-methyl-1H-imidazole-2-yl)thio]phenyl}amino)-6-methoxy-7-(4-morpholin-4-ylpiperidin-1-yl)quinoline-3-carbonitrile, 4-({3-Chloro-4-[(1-methyl-1H-imidazole-2-yl)thio]phenyl}amino)-6-methoxy-7-[4-(1-methylpiperidin-4-yl)pipiperazin-1-yl]quinoline-3-carbonitrile, and 4-({3-Chloro-4-[(1-methyl-1H-imidazole-2-yl)thio]phenyl}amino)-7-{4-[2-(1H-imidazole-1-yl)ethyl]piperazin-1-yl}-6-methoxyquinoline-3-carbonitrile, or a crystalline form or a pharmaceutically acceptable salt thereof.

5. The method of treating a melanoma, a pancreatic cancer, a colon cancer and a lung cancer in a mammal comprising administering a compound of formula 1.

6. The method of claim 5 further comprising providing the mammal with an effective amount of at least one anti-cancer agent.

7. The method of claim 6 wherein the at least one anticancer agent is provided prior to the at least one pharmaceutical composition, concurrently with the at least one pharmaceutical composition or after the at least one pharmaceutical composition.

8. A means for preparing a compound of Formula I, of claim 1 comprising:

a. reacting a compound of Formula 2

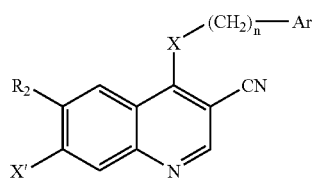

2 with heated $R_3$—H, where H is bound to $R_3$ via a nitrogen atom;
optionally with a base;
b. to yield the compound of Formula 1 of claim 1,

1 wherein:
X' is fluoro or chloro provided that when X' is chloro, $R_2$ is nitro.

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: HUMAN

<400> SEQUENCE: 1

Ala Pro Arg Thr Pro Gly Gly Arg Arg
1               5

<210> SEQ ID NO 2
<211> LENGTH: 16
<212> TYPE: PRT
<213> ORGANISM: HUMAN

<400> SEQUENCE: 2

Lys Lys Phe Glu Leu Leu Pro Thr Pro Pro Leu Ser Pro Ser Arg Arg
1               5                   10                  15